United States Patent [19]

Lockhoff et al.

[11] Patent Number: 4,855,283

[45] Date of Patent: Aug. 8, 1989

[54] NOVEL PHARMACEUTICALLY ACTIVE N-(2-AMINOACYLAMIDO-2-DEOXY-HEXOSYL)-AMIDES, -CARBAMATES AND -UREAS

[75] Inventors: Oswald Lockhoff, Cologne; Yutaka Hayauchi, Leverkusen; Peter Stadler, Haan; Klaus G. Stünkel; Gert Streissle, both of Wuppertal; Arnold Paessens, Haan; Volker Klimetzek, Velbert-Toenisheide; Hans-Joachim Zeiler, Velbert; Karl G. Metzger; Hein-Peter Kroll, both of Wuppertal; Helmut Brunner, Langenfeld; Klaus Schaller, Wuppertal, all of Fed. Rep. of Germany

[73] Assignee: Bayer Aktiengesellschaft, Leverkusen, Fed. Rep. of Germany

[21] Appl. No.: 874,983

[22] Filed: Jun. 16, 1986

[30] Foreign Application Priority Data

Jun. 20, 1985 [DE] Fed. Rep. of Germany ....... 3521994

[51] Int. Cl.$^4$ .................... A61K 37/00; C07K 9/00
[52] U.S. Cl. ........................ 514/8; 530/322; 536/17.9; 514/25; 424/88; 424/89
[58] Field of Search ............. 530/322; 514/8, 25; 424/88, 89; 536/17.9

[56] References Cited

U.S. PATENT DOCUMENTS

4,574,122  3/1986  Krüger et al. ............... 536/22

FOREIGN PATENT DOCUMENTS

0091645 10/1983  European Pat. Off. .

OTHER PUBLICATIONS

Yoshimura et al., "Studies on 2-amino-2-deoxy-D-glucose Derivatives", Carbohydrate Research, 5 (1967) pp. 82–92.
Yoshimura et al., Chemical Abstracts, vol. 68, 1968, p. 316, No. 3163y.
Cran et al., Organic Chemistry, 2nd Ed., 1964, p. 361.

Primary Examiner—Johnnie R. Brown
Assistant Examiner—Elli Peselev

Attorney, Agent, or Firm—Sprung Horn Kramer & Woods

[57] ABSTRACT

Compounds of the formula

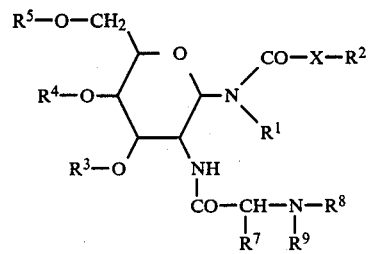

in which $R^1$ denotes hydrogen or a saturated or singly or multiply unsaturated alkyl radical having up to 50 carbon atoms, X represents —$CH_2$—, —O— or —NH—, $R^2$ denotes hydrogen or a saturated or singly or multiply unsaturated alkyl radical having up to 50 carbon atoms, $R^3$, $R^4$ and $R^5$, independently of one another, denotes hydrogen or acyl—CO—$R^6$, $R^6$ being an alkyl radical having up to 10 carbon atoms, $R^7$ denotes hydrogen, $C_1$-$C_7$-alkyl-, hydroxymethyl, 1-hydroxyethyl, mercaptomethyl, 2-(methylthio)-ethyl, 3-aminopropyl, 3-ureidopropyl, 3-quanidylpropyl, 4-aminobutyl, carboxymethyl, carbamylmethyl, 2-carboxyethyl, 2-carbamoylethyl, benzyl, 4-hydroxybenzyl, 3-indolylmethyl or 4-imidazolylmethyl, and $R^8$ represents hydrogen or methyl, and $R^9$ represents hydrogen, acetyl, benzoyl, trichloroacetyl, trifluoroacetyl, methoxycarbonyl, t-butyloxycarbonyl or benzyloxycarbonyl and $R^7$ and $R^8$ together can denote —$CH_2$—$CH_2$—$CH_2$, and pharmaceutically acceptable salts thereof stimulate the immune system and can be used in conjuction with antibiotics and vaccines. New intermediates are also shown.

24 Claims, No Drawings

NOVEL PHARMACEUTICALLY ACTIVE N-(2-AMINOACYLAMIDO-2-DEOXY-HEXOSYL)-AMIDES, -CARBAMATES AND -UREAS

The invention relates to new N-glycosylamides, N-glycosylureas and N-glycosylcarbamates, each of which is substituted in the sugar residue by an amino acid, and to processes for their preparation and to their use as medicaments.

The new compounds correspond to the general formula I

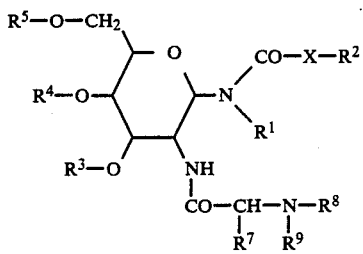

in which $R^1$ denotes hydrogen or a saturated or singly or multiply unsaturated aliphatic hydrocarbon radical having up to 50 carbon atoms, X represents —$CH_2$—, —O— or —NH—, $R^2$ denotes hydrogen or a saturated or singly or multiply unsaturated aliphatic hydrocarbon radical having up to 50 carbon atoms, $R^3$, $R^4$ and $R^5$, independently of one another, denote hydrogen or acyl—CO—$R^6$, $R^6$ being understood to be an alkyl radical having one to 10 carbon atoms, $R^7$ denotes hydrogen, $C_1$-$C_7$-alkyl, hydroxymethyl, 1-hydroxymethyl, mercaptomethyl, 2-(methylthio)-ethyl, 3-aminopropyl, 3-ureidopropyl, 3-guanidylpropyl, 4-aminobutyl, carboxymethyl, carbamoylmethyl, 2-carboxyethyl, 2-carbamoylethyl, benzyl, 4-hydroxybenzyl, 3-indolylmethyl or 4-imidazolylmethyl, and $R^8$ denotes hydrogen or methyl, and $R^9$ represents hydrogen, methyl, acetyl, benzoyl, trichloroacetyl, trifluoroacetyl, methoxycarbonyl, t-butyloxycarbonyl or benzyloxycarbonyl and $R^7$ and $R^8$ together can denote —$CH_2$—$CH_2$—$CH_2$—

The stereochemistry at the chiral center in the α-amino acid is either L or R.

The radical $R^1$ preferably represents a straight-chain or branched, saturated or unsaturated alkyl radical having up to 20 C atoms, particularly preferably, having 10 to 20 C atoms.

Examples of straight-chain saturated alkyl radicals $R^1$ are methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl, docosyl, tetracosyl, hexacosyl, octacosyl and triacontyl.

Examples of unsaturated radicals $R^1$ are vinyl, allyl, 2-butenyl, 3-butenyl, 2-hexenyl, 3-hexenyl, 4-hexenyl, 5-hexenyl, 2-octenyl, 4-octenyl, 6-octenyl, 7-octenyl, 2-decenyl, 4-decenyl, 6-decenyl, 8-decenyl, 9-decenyl, 2-dodecenyl, 6-dodecenyl, 10-dodecenyl, 11-dodecenyl, 4-tetradecenyl, 6-tetradecenyl, 10-tetradecenyl, 6-hexadecenyl, 8-hexadecenyl, 10-hexadecenyl, 12-hexadecenyl, 6-heptadecenyl, 8-heptadecenyl, 10-heptadecenyl, 6-octadecenyl, 8-octadecenyl, 10-octadecenyl, 8,11-heptadecanedienyl or 8,11,14-heptadecanetrienyl.

In general, among the unsaturated radicals those with longer chains are preferred, especially the singly or doubly unsaturated having 10 to 20 carbon atoms.

The radicals $R^1$ can also be branched, saturated or singly or doubly unsaturated alkyl radicals. In this context, the preferred alkyl substituents of the alkyl or alkenyl chain are those alkyl radicals which have up to 12 carbon atoms.

Examples of branched alkyl radicals $R^1$ are 2-methyldodecyl, 4-methyldodecyl, 6-methyldodecyl, 8-methyldodecyl, 11-methyldodecyl, 4-ethyldodecyl, 8-ethyldodecyl, 2-methyltetradecyl, 4-methyltetradecyl, 10-methyltetradecyl, 13-methyltetradecyl, 2-methylhexadecyl, 4-methylhexadecyl, 8-methylhexadecyl, 15-methylhexadecyl, 1-methyloctadecyl, 2-methyloctadecyl, 4-methyloctadecy, 10-methyloctadecyl, 16-methyloctadecyl, 17-methyloctadecyl, 1-butyldodecyl, 1-dodecyldodecyl, 1-decyltetradecyl and 1-dodecylhexadecyl.

The radical $R^2$ preferably represents hydrogen or a straight-chain or branched, saturated or unsaturated alkyl radical having up to 20 C atoms, particularly preferably having 8 to 20 C atoms.

Examples of the radicals $R^2$ are the radicals mentioned for $R^1$.

As can be seen from Formula 1 the compounds according to the invention are based on a substituted 2-amino-2-deoxyhexose. These sugars are always N-glycosidically bonded via C-1, the anomeric carbon atom, to the acylamido, carbamido or alkoxycarbonylamido group

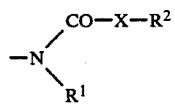

with the abovementioned meanings for $R^1$, $R^2$ and X.

Preferred amino sugars in the compounds according to the invention, of the formula I, are 2-amino-2-deoxy-D-glucose and 2-amino-2-deoxy-D-galactose.

The 2-amino group of the said amino sugars in the compounds according to the invention, of the formula I, is amidically bonded to an α-amino acid or an α-amino acid derivative.

Preferred amino acids are the natural L-amino acids such as glycine, sarcosine, hippuric acid, alanine, valine, leucine, isoleucine, serine, threonine, cysteine, methionine, ornithine, citrulline, arginine, aspartic acid, asparagine, glutamic acid, glutamine, phenylalanine, tyrosine, proline, tryptophan and histidine. However, it is also possible for D-amino acids, such as D-alanine, or amino carboxylic acids, such as α-aminobutyric acid, α-aminovaleric acid, α-aminocaproic acid or α-aminoheptanoic acid, both in the D- and the L-form, to act as substituents on the amino sugar.

The invention also relates to processes for the preparation of the compounds according to formula I. This entails starting from a 2-amino-2-deoxyglycopyranose derivative II, which is protected on the amino group,

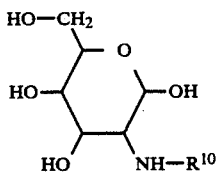

in which

R[10] represents a protective group for the protection of amino groups, which is known from the synthesis of peptides and can, where appropriate, be selectively eliminated.

Examples of suitable protective groups are acyl groups, such as trifluoroacetyl or trichloroacetyl, o-nitrophenylsulphenyl, 2,4-dinitrophenylsulphenyl or optionally substituted lower alkoxycarbonyl, such as methoxycarbonyl, t-butyloxycarbonyl, benzyloxycarbonyl, p-methoxybenzyloxycarbonyl or 2,2,2-trichloroethyloxycarbonyl groups, that is to say, in general, those groups which in peptides can be selectively eliminated again. Suitable N-protected amino-hexose derivatives II are known in principle (literature, for example, M. Bergmann and L. Zervas, Ber. 64, 975 (1931); D. Horton, J. Org. Chem. 29, 1776 (1964); P. H. Gross and R. W. Jeanloz, J. Org. Chem. 32, 2759 (1967); M. L. Wolfrom and H. B. Bhat, J. Org. Chem. 32, 1821 (1967); general: J. F. W. McOmie (Editor). Prot. Groups. Org. Chem., Plenum Press (1973); Geiger in "The Peptides" Vol. 3, p 1-99, (1981) Academic Press; and Literature cited there).

Particularly preferred amino protective groups for the preparation of the compounds according to formula I are the BOC group (tert. butyloxycarbonyl) or the Z group (benzyloxycarbonyl).

The blocked amino sugar derivatives II are reacted, in a first reaction step, with amines III,

where

R[1] has the abovementioned meaning, to give glycosylamines IV

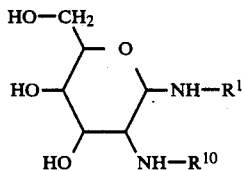

Glycosylamine preparations of this type are known in principle (ELLIS, Advances in Carbohydrate Chemistry 10, 95 (1955)) and are, specifically, described in DE-OS (German Published Specification) No. 3,213,650.

In the second reaction step, the glycosylamines IV are reacted either with suitable carboxylic acid derivatives V, such as carboxyl halides, or carboxylic anhydrides,

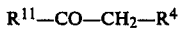

R[2] having the abovementioned meaning, and R[11] representing halogen such as, for example, chlorine, or representing —O—CO—R[2] with the abovementioned meaning for R[2], or representing —O—CO—O-lower alkyl. In this way, glycosylamides VI

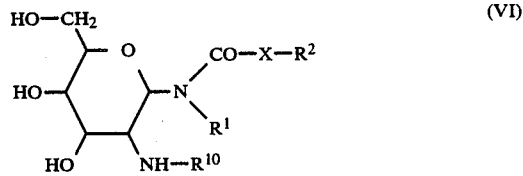

in which

R[1], R[2] and R[10] have the abovementioned meanings, and X represents —CH$_2$—, are obtained.

The conditions for N-acylations of this type are indicated in DE-OS (German Published Specification) No. 3,213,650.

In a preferred embodiment, the glycosylamines of the formula IV are reacted with one to two equivalents of a carbonyl chloride V or with one to two equivalents of a mixed anhydride which has been obtained from the relevant carboxylic acid R[2]—CH$_2$—CO$_2$H and ethyl chloroformate or isobutyl chloroformate, in the presence of an organic auxiliary base, by methods known from the literature, to give the glycosylamide VI with X=—CH$_2$—.

This is carried out in organic or aqueous-organic solvents between 0° C. and 50° C., where appropriate in the presence of an inorganic or organic base. Suitable diluents are alcohols, such as methanol, ethanol, 1-propanol or 2-propanol, or ethers, such as diethyl ether, tetrahydrofuran or 1,4-dioxane, or halogenated hydrocarbons, such as dichloromethane, trichloromethane or 1,2-dichloroethane, or N,N-dimethylformamide.

When the glycosylamines IV which are obtained in the first step are reacted with halogenoformic esters VII

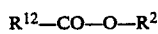

R[12] representing halogen such as, for example, chlorine or bromine, and R[2] having the abovementioned meaning, then glycosylcarbamates VI are obtained, R[1], R[2] and R[10] in formula VI having the abovementioned meaning, and X in formula VI representing oxygen.

In a preferred embodiment, the glycosylamines of the formula VI are reacted with one to two equivalents of a chlorocarbonic ester VII to give the glycosylcarbamate. This is preferably carried out in organic or aqueous-organic solvents at temperatures between 0° C. and 50° C., but particularly preferably at room temperature. Suitable solvents are alcohols, ethers, halogenated hydrocarbons or dimethylformamide, such as are mentioned above.

When glycosylamines IV which are obtained in the first step are reacted with one to two equivalents of an organic isocyanate VIII

R[2] having the abovementioned meaning, glycosylureas of the formula VI are obtained, R[1], R[2] and R[10] ureas of the abovementioned meanings and X representing —NH—.

This acylation reaction is, like the abovementioned reactions, preferably carried out in organic solvents, the reaction temperatures being between −20° C. and 60° C., preferably between 0° C. and 25° C.

Suitable solvents are the abovementioned alcohols, ethers, halogenated hydrocarbons, or dimethylformamide.

The glycosylamides (VI, X=—CH₂—), glycosylcarbamates (VI, X=—O—) or glycosylureas (VI, X=—NH—) obtained in this way are isolated in the form of crystalline or amorphous solids by processes known per se and, if necessary, are purified by recrystallization, chromatography, extraction, etc.

In many cases, it is also advantageous to carry out, in parallel with or in place of the abovementioned purification steps, a chemical derivatization which leads to a derivative of the glycosylamides, -carbamates and -ureas VI, with the abovementioned meanings for $R^1$, $R^2$, $R^{10}$ and X, which has good crystallization properties. Chemical derivatization of this type are, in the case of the glycosylamides, glycosylcarbamates and glycosylureas according to the invention, for example esterification reactions on the hydroxyl groups of the sugar residues.

Examples of suitable ester groups are acetyl, benzoyl or p-nitrobenzoyl groups.

To prepare the tri-O-acyl derivatives of the glycosylamides, glycosylureas or glycosylcarbamates, the corresponding triols VI are reacted with acylating agents in the presence of inorganic or organic auxiliary bases. Suitable acylating agents are acid chlorides, such as acetyl chloride, benzoyl chloride or p-nitrobenzyl chloride, or anhydrides, such as, for example, acetic anhydride. This results in the formation of the esters according to formula IX

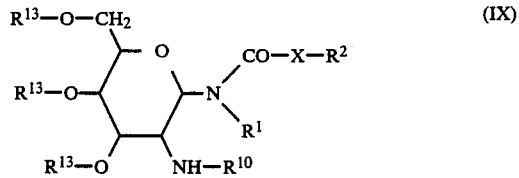

$R^1$, $R^2$, $R^{10}$ and X having the abovementioned meanings, and $R^{13}$ representing acetyl, benzoyl or p-nitrobenzoyl.

The O-acylation reactions are preferably carried out in inert organic solvents. Those which may be mentioned are halogenated hydrocarbons, such as dichloromethane, trichloromethane or 1,2-dichloroethane, ethers, such as tetrahydrofuran, or 1,4-dioxane, esters, such as ethyl acetate, and amides, such as dimethylformamide.

It is also possible for the organic bases alone, such as triethylamine or pyridine, to be indicated as suitable solvents.

The bases which can be used are all the bases used in organic chemistry for O-acylations. Preferably, triethylamine, pyridine or the mixture pyridine/4-dimethylaminopyridine are used.

The triesters IX can be readily crystallized from organic solvents. Particularly preferred for the crystallization are polar solvents, such as short-chain alcohols, that is to say methanol, ethanol, n-propanol or isopropanol. Other solvents suitable for the crystallization of the triesters IX are mixtures of organic solvents with polar inorganic or organic solvents, for example tetrahydrofuran-methanol, tetrahydrofuran-water, ethanol-water, and isopropanol-water.

The triesters IX which have been purified by single or, where appropriate, multiple recrystallization are returned to the triols VI by hydrolysis or transesterification of the three O-acetyl groups.

A multiplicity of types of ester cleavages are known in organic chemistry. For the preparation of the triols VI from the triesters IX mentioned may be made of the transesterification of the acyl groups in the presence of methanol and catalytic amounts of sodium methanolate, which is known as the ZEMPLEN hydrolysis in organic chemistry.

The third reaction step in the preparation of the compounds according to the invention, of the formula I, comprises the selective cleavage of the protective group of the 2-amino group on the sugar in the compounds of the formula VI. In this reaction, particular care has to be taken that there is no simultaneous elimination of the 1-amido or the 1-carbamido or of the 1-(alkoxycarbonylamido) group on the sugar in the compounds of the formula VI.

The benzyloxycarbonyl group, which is preferably used, on C-2 of the aminohexanes can be quantitatively and selectively cleaved, with retention of the 1-amido, 1-carbamido or 1-alkoxycarbonylamido group, under the conditions of hydrogenolysis. This hydrogenolysis provides the glycosylamides, glycosylureas or glycosylcarbamates with a free 2-amino group on the sugar with the following structural formula X

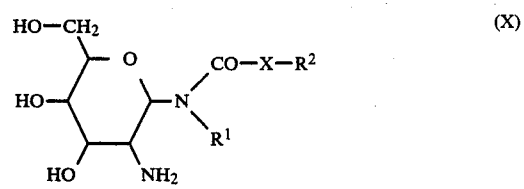

with the abovementioned meanings for $R^1$, $R^2$ and X.

Examples of suitable catalysts for the hydrogenolysis are noble metals such as platinum or palladium which are adsorbed onto active charcoal.

Palladium/charcoal (5% or 10%) is preferably used. The hydrogenolysis can be carried out under atmospheric pressure or elevated pressure in a suitable pressure vessel. Inert solvents are suitable as solvents for the hydrogenation, such as, for example, alcohols such as methanol, ethanol, propanol, ethers such as tetrahydrofuran or 1,4-dioxane, or carboxylic acids such as acetic acid, or mixtures of the said solvents in question, where appropriate with addition of water or dilute acids such as hydrochloric acid or sulphuric acid. Of course, when acids are added the 2-amino-2-deoxy-glycosylamides, -carbamates and -ureas according to formula X result as the ammonium salts of these acids.

The t-butyloxycarbonyl protective group, which is likewise preferably used, in the compounds of the formula VI can be cleaved by methods known from the literature using mineral acids such as hydrochloric acid or sulphuric acid.

In this case too, the 2-amino-2-deoxy-glycosylamides, -carbamates and -ureas of the formula X are selectively obtained, and they then result as ammonium salts of the acids used for the cleavage.

The fourth reaction step for the synthesis of the compounds according to the invention, of the formula I, comprises the linkage of the aminoglycosylamides, amides, -carbamates or -ureas according to formula X, or of their salts, with a suitable amino acid derivative.

Suitable amino acid derivatives are N-blocked amino acids XI

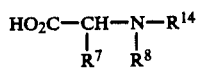

$R^7$ having the abovementioned meaning,
$R^8$ representing hydrogen or methyl, and
$R^{14}$ representing a protective group which is customarily used in peptide synthesis and can be selectively eliminated again while retaining the peptide bond.

The protective groups for the amino group in formula XI which are preferably used are the abovementioned, and the benzyloxycarbonyl or t-butyloxycarbonyl group are particularly preferred.

The linkage of the 2-amino-2-deoxy-glycosylamide, -carbamate or -urea of the formula X with an amino acid derivative of the formula XI can be carried out by conventional methods of peptide synthesis (E. Wünsch et al.: Synthese von Peptiden (Synthesis of peptides) in: Methoden der Org. Chemie (Methods of org. chemistry) (Houben-Weyl) (E. Müller, Editor), Vol XV/1 and XV/2, 4th Edition, published by Thieme, Stuttgart (1974).

Examples of conventional processes are the condensation of the amino group in the compound of the formula X with an amino acid derivative XI in the presence of water-removing agents, for example dicyclohexylcarbodiimide or diisopropylcarbodiimide.

The condensation of the compounds of the formula X with those of the formula XI can also be carried out when the carboxyl group is activated. A possible activated carboxyl group is, for example, an acid anhydride, preferably a mixed anhydride, such as an acetate of the acid, or an amide of the acid, such as an imidazolide, or an activated ester. Examples of the activated esters are cyanomethyl esters, pentachlorophenyl esters, and N-hydroxyphthalimide esters. Activated esters can also be obtained from the acid XI and N-hydroxysuccinimide or 1-hydroxybenzothiazole in the presence of a water-removing agent, such as carbodiimide.

The derivatives of the amino acids are known and can be prepared in a known manner.

The condensation of the amino compound X with the optionally activated carboxyl compounds XI provides the peptidoglycolipids of the formula XII

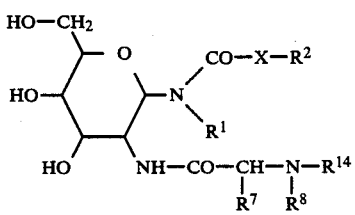

with the abovementioned meanings for $R^1$, $R^2$, $R^7$, $R^8$, $R^{14}$ and X.

In a final process step for the preparation of the compounds according to formula I, the protective group $R^{14}$ in the compounds of the formula XII is eliminated.

Care has to be taken during this that the other amide, urethane or urea groups present in the compounds of the formula XII are not cleaved.

The protective groups $R^{14}$ which are preferably used in the compounds of the formula XII, the N-carbobenzoxy group and the N-tert.-butyloxycarbonyl group, can be eliminated while retaining the amide, urethane or urea group.

The carbobenzoxy group can be selectively eliminated by hydrogenolysis in the presence of noble metals such as, for example, palladium on charcoal, in a suitable solvent such as ethanol, methanol, glacial acetic acid or tetrahydrofuran, whether as the pure solvent or combined with one another or with water, it being possible to carry this out both under atmospheric pressure and under elevated pressure.

The tert.-butyloxycarbonyl group $R^{14}$ in the compounds of the formula XII can be eliminated by acidolytic processes. Examples of suitable conditions are the use of hydrogen chloride in suitable solvents such as, for example, glacial acetic acid, diethyl ether, dioxane or ethyl acetate, at room temperature.

Processes of this type for the cleavage of the t-butyl carbamates are known in principle.

The peptidoglycosylamides, -carbamates and -ureas of the formula I, which are obtained in this manner, are isolated in the form of crystalline or amorphous solids, by processes known per se, and are, if necessary, purified by recrystallization, chromatography, extraction etc.

The compounds according to the invention, of the formula I, can also be prepared by a second synthetic route with similarly good results.

This second synthetic route differs from the first, which is described above, in that the sequence of the linkage of the synthons amino sugar, amino acid, amine $R^1$—$NH_2$ and carboxylic acid $R^2$—$CH_2$—$CO_2$—H, or carbonic acid derivative $R^2$—O—CO—halogen, or $R^2$—NCO, with the abovementioned meanings of $R^1$ and $R^2$, is different.

In this second route, suitable 2-N-(aminoacyl)aminosugars of the formula XIII

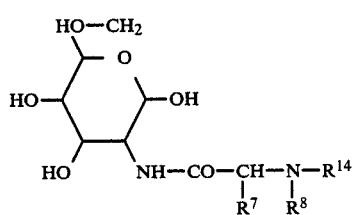

with the abovementioned meaning for $R^7$ and $R^8$, and in which $R^{14}$ represents an amino protective group known in peptide chemistry, preferably the benzyloxycarbonyl or the t-butyloxycarbonyl group, are used as the starting component.

The preparation of 2-aminoacyl-aminosugars of this type is known in principle (for example MIYAZEKI et al., Yakugaku Zasshi, 100, (1980) 95).

The compounds of the formula XIII which are thus obtained are then condensed with amino compounds of the formula III to give glycosylamines of the general formula XIV

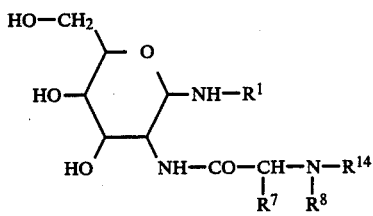

(XIV)

$R^1$, $R^7$, $R^8$ and $R^{14}$ having the abovementioned meaning.

All the processes described above for the preparation of the compounds of the general formula IV can be used for the preparation of the compounds of the general formula XIV.

The compounds of the formula XIV are then reacted either with the abovementioned carboxylic acid derivatives V or with halogenoformic esters VII or with organic isocyanates VIII to give the 2-(aminoacyl)-aminoglycosylamides of the formula XII (X=—CH$_2$—) or the -carbamates of the formula XII (X=—O—) or the -ureas of the formula XII (X=—NH—). These acylation reactions can generally be carried out by the processes described above for the reaction of glycosylamines with carboxylic or carbonic acid derivatives.

The intermediates XII which are obtained in this way can be purified by the abovementioned physical purification method. However, it is preferble to convert the compounds XII, by the methods of O-acylation described above, into the tri-O-acetates or the tri-O-benzoates of the general formula XV

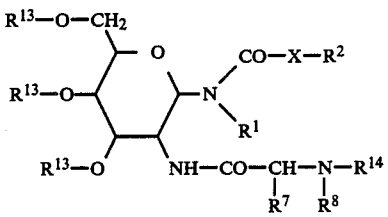

(XV)

with the abovementioned meanings for $R^1$, $R^2$, $R^7$, $R^8$, $R^{13}$, $R^{14}$ and X.

These compounds can readily be crystallized, preferably from polar solvents such as methanol or ethanol, and thus purified.

The purified crystalline derivatives XV are then converted into the triols XII by the abovementioned methods of ester hydrolysis, which are widely used especially in sugar chemistry.

The final elimination of the protective groups in the amino acid in the compounds of the formula XII has already been described above for the preparation of the compounds of the formula I.

The processes according to the invention for the preparation of the compounds of the formula I can be represented diagrammatically as follows:

1st Process

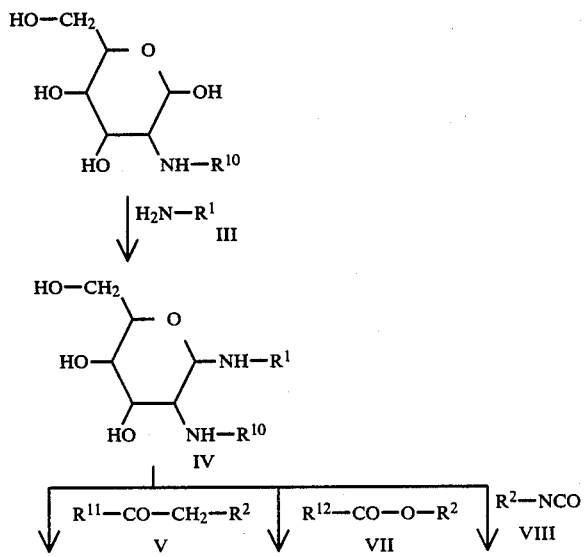

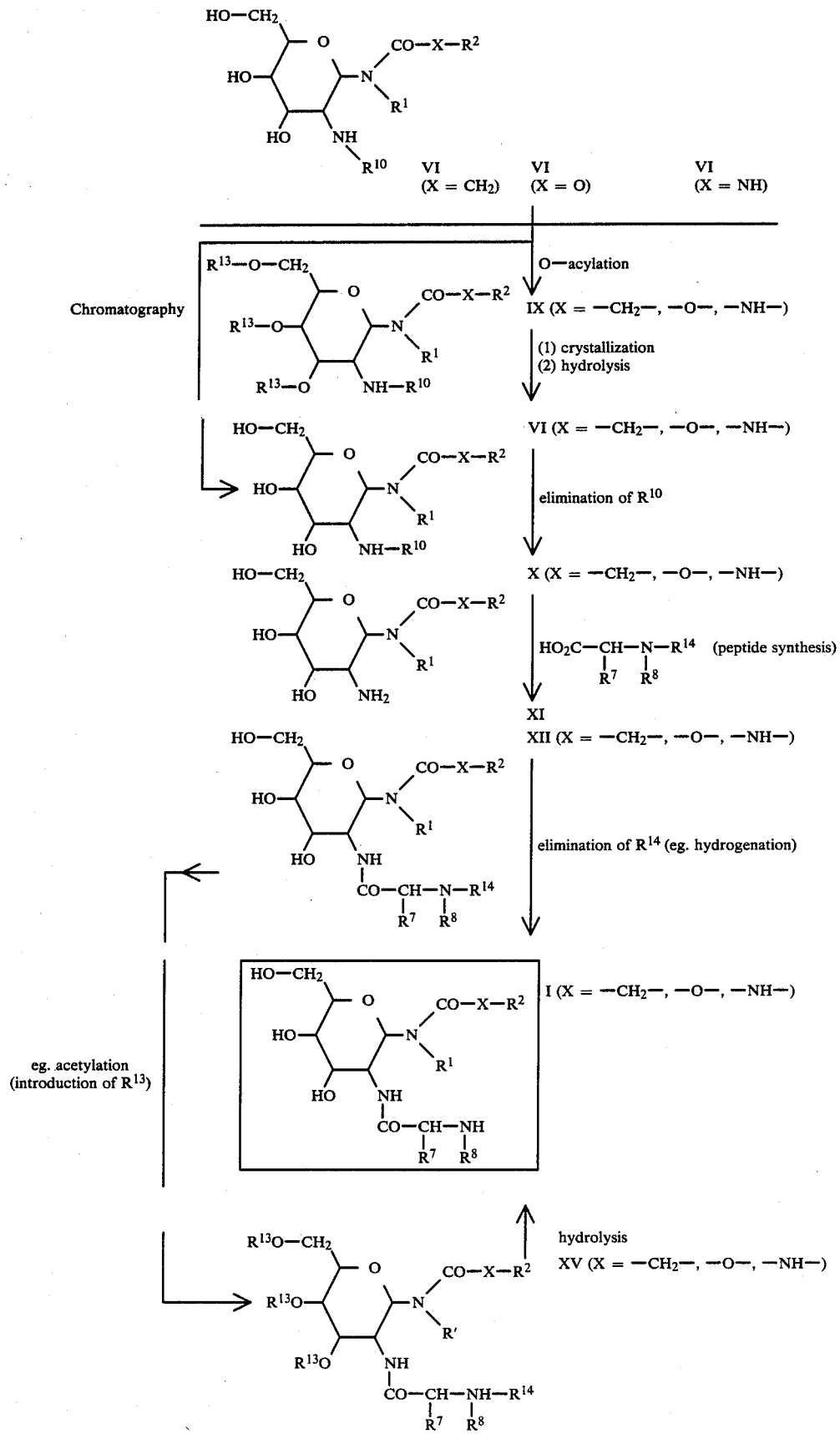

2nd process

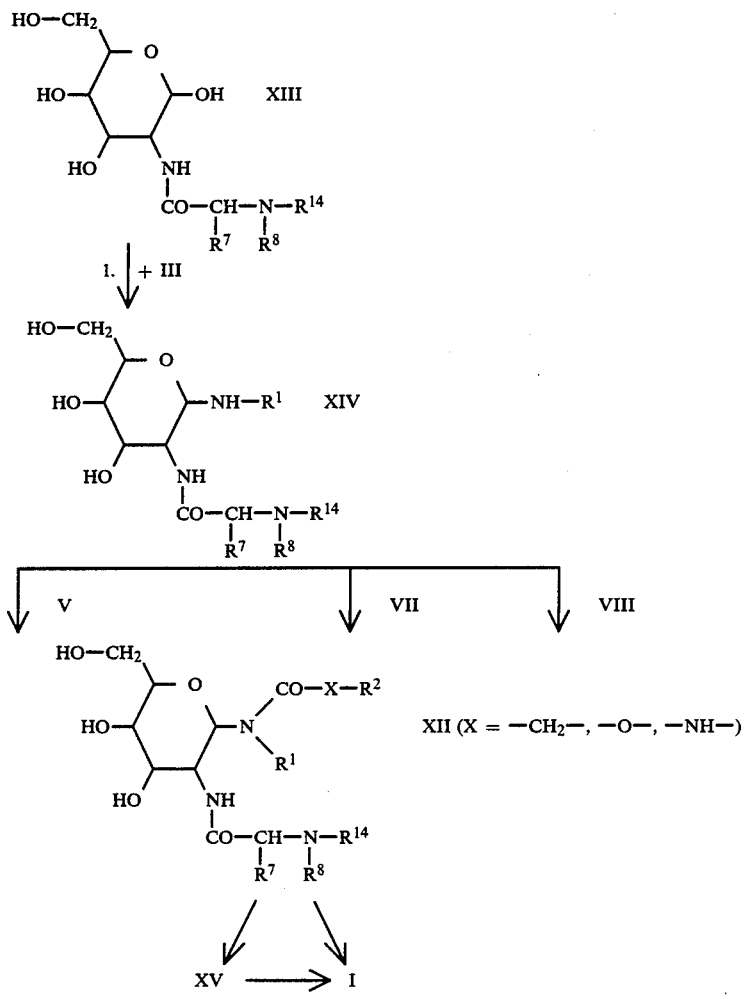

The invention also relates to salts of the compounds of the formula I. These are primarily the non-toxic salts which can customarily be used in pharmacy, for example chlorides, acetates and lactates, or inert salts of the compounds of the formula I.

The compounds of the invention exhibit a pronounced resistance-increasing action. It has been found that the class of compounds increases, in an antigen-specific manner, the antibody synthesis by the immune system, and, moreover, potentiates the non-specific resistance inherent to the host. These results were obtained using the following design of experiments.

Increase in the primary humoral immunity in vitro towards sheep erythrocytes (SE).

It is experimentally possible to induce in vitro the development of a humoral immune response with heterologous red blood cells by primary immunization of mouse spleen cells in suspension cultures (R. I. Mishell and R. W. Dutton, J. Exp. Med. 126, 423 (1967)).

For this purpose, Balb/c mouse spleen cells are cultivated for five days in the presence of antigen (SE) and test substance. The cells are harvested, washed and plated out together with the antigen and complement in semi-solid agar and incubated at 37° C. for two hours (N. K. Jerne, A. A. Nordin and C. Henry, "Cell bound Antibodies", eds. Amos and Koprowski, Wistar Inst. Press, Philadelphia, USA, pp 109 (1963)). The antigen-sensitization of mouse lympho-cytes in the primary culture leads to synthesis and release of antibodies. The specific antibodies which are secreted bind to the SE antigen and lyse these cells owing to the presence of complement (plaque formation). Substances of the present class of compounds are able to increase, as a function of the dose in the range 0.3–100 $\mu$g/ml, the number of antibody-forming cells (Table 1).

TABLE 1

Action of various selected peptidoglycolipid analogues of the present class of compounds on antibody synthesis in vitro

| Substances Example No. | Antibody-secreting cells/culture as a function of the dose ($\mu$g/ml) | | | | | |
|---|---|---|---|---|---|---|
| | 0 | 1 | 3 | 10 | 30 | 100 |
| M 61 | 1595 | 2600 | 2190 | 7380 | 10,200 | 9920 |
| M 34 | 1710 | 2450 | 5700 | 8260 | 6240 | 10,640 |
| M 66 | 1710 | 1390 | 3480 | 6160 | 7600 | 8640 |
| M 51 | 1710 | 1260 | 3560 | 5560 | 7600 | n.d.[1] |
| M 54 | 1595 | 1910 | 2230 | 6160 | 6460 | n.d.[1] |

[1]not done

Increase in the primary humoral immunity in vivo towards the soluble antigen ovalbumin.

NMRI mice were immunizied subcutaneously (s.c.) with a suboptimal dose of antigen (1 μg/animal, day 0). With suboptimal antigen stimulation, only a small number of lymphocytes of the animals are stimulated to synthesize antibodies. The additional treatment of the animals with compounds of the said examples of the present invention is able significantly to increase the antibody titre in the serum of the animals on single subcutaneous administration of 0.3–30 mg/kg. The determination of the antibody titre is carried out by indirect haemagglutination on day 10. The effect of the treatment is expressed by the geometric mean of $\log_2$ of the titre (Table 2).

In contrast to other immunostimulants, for example bacterial, such as LPS from Gram-negative bacteria, the immunostimulant effect of the said compounds is antigen-dependent, that is to say surprisingly the substances bring about an increase in antibody synthesis only in association with an antigenic stimulus (in this case SE or ovalbumin). In contrast to the conventional immunostimulants mentioned, they have no mitogenic properties.

The compounds according to the invention also bring about an increase in the state of activity of macrophages in vitro and in vivo. The increased state of activation can be detected by the increase in the antimicrobial efficiency of the macrophages in vitro.

TABLE 2
Adjuvant action of various compounds according to the invention in vivo, with the soluble antigen ovalbumin as example

| Substances Example No. | Haemagglut. titre ($\log_2$) Dose (mg/kg) | | | |
|---|---|---|---|---|
| | 0 | 3 | 10 | 30 |
| M 17 | 4.2 | 4.4[1] | 5.6 | 6.6 |
| M 34 | 4.8 | 5.6[1] | 6.2 | 7.2 |
| M 1 | 5.4 | 5.4[1] | 6.4 | 7.6 |
| M 41 | 4.2 | 5.6 | 5.4 | 6.6 |
| M 66 | 4.0 | 6.2 | 6.6 | 7.2 |
| M 74 | 4.4 | 5.8 | 6.6 | 7.0 |

[1]not significant;
the other figures show significant increases ($p \leq 0.05$)

The compounds according to the invention are able, on the one hand, to increase the immunogenicity of an antigen when mixed with it and, on the other hand, to increase the immunological reactivity of the treated organism on systemic administration. This entails the substances mentioned being able to activate the lymphocytes which are responsible for the formation of antibodies.

Thus, the new compounds can be used as adjuvants mixed with vaccines in order to improve the success of vaccination and to increase the protection conferred by immunity against infection by bacterial, viral or parasitic pathogens.

Furthermore, the compounds described are suitable, when mixed with a very wide variety of antigens, as adjuvants in the experimental and industrial preparation of antisera for therapy and diagnosis.

Description of Experiments

Adjuvant action on administration of virus vaccines

Herpesvirus vaccine:

Rabbit kidney cells were cultured by the method of N. J. Schmidt (in: Viral, Rickettsial and Chlamydial Infections, E. H. Lennette and N. J. Schmidt, Editors, p. 89, American Public Health Association, Inc., Washington, 1979) with Minimum Essential Medium Eagle (MEME) and 10% calf serum as the nutrient medium. As soon as a confluent cell lawn had formed, the cell cultures were infected with herpes simplex virus type I (HSV I). 48 hours after the infection, cell cultures and nutrient medium were frozen at $-80°$ C., thawed and centrifuged at low speed. The cell culture supernatant, which contained $10^7$ $CCID_{50}$[1], was removed and frozen at $-80°$ C. until used.

[1]Cell-culture infectious doses

The method of Spear et al. (Journal of Virology 9, 143–159 (1972)), with modifications, was used for the purification of HSV I.

Cell culture supernatants containing HSV I were pelletted by ultracentrifugation (4° C.) at 40,000 rpm in a T145 rotor for one hour.

The virus-containing pellets were taken up in a small volume of 0.01M tris buffer, pH 7.5, and sonciated (5×, 2 sec; Branson Sonifier).

The sample was adjusted to 50% sucrose (w/w), and 10 ml portions were placed in 38 ml centrifuge tubes for centrifugation in a SW28 rotor. The discontinuous gradient was prepared by the method of Spears (see above), centrifuged and harvested.

The subsequent concentration of the virus by ultracentrifugation was carried out via a sucrose pad which was adjusted to 1M urea.

The resulting pellet was taken up in 0.01M tris buffer, pH 7.4, sonicated and adjusted to an extinction $E^{280}$ of about 2–3 mg/ml.

The viral "envelope" antigen (EAG) was then isolated from the purified virus by modification of the methods of Klein et al. (Archives of Virology 68, 73–80 (1981). Purified virus with an extinction of $E^{280}=2.8$ mg/ml was adjusted to 1% triton-x-100, and incubated at 4° C. overnight. The detergent-treated virus was placed on a potassium tartrate gradient (5–40%) in 0.01M tris buffer, pH 7.4, and centrifuged in a SW28 rotor at 28,000 rpm for 18 hours.

Samples from the upper third of the gradient, with an absorption greater than 0.1 at 280 nm, were combined, concentrated by vacuum dialysis, dialyzed against PBS, and frozen at $-80°$ C. until used.

The complete HSV I obtained from the rabbit kidney cells was inactivated at 60° C. for four hours. The complete, inactivated HSV I and the EAG were used for immunization of mice against infection with HSV I.

Pseudorabies virus vaccine

Pseudorabies virus was cultured by the method of E. A. Rollinson and G. White (Antimicrob. Ag. Chemother, 24, 221–226, 1983) in PK-15 cells, an established cell line from pig kidneys, which were obtained from the American Type Culture Collection, Washington, with MEME and 2% serum from newborn calves as the nutrient medium. As soon as cell damage caused by viruses appeared, the cell cultures and nutrient medium were frozen at $-80°$ C., thawed and centrifuged at a low speed. The cell culture supernatant, which contained $10^8$ $CCID_{50}$ pseudorabies virus, was removed and frozen at $-80°$ C.

Pseudorabies virus was concentrated and purified by the method of Ben-Porat et al. (Virology 41, 256–64, 1970). The viral "envelope" antigen (EAG) was then isolated from the purified virus by the method of A. S. Kaplan and T. Ben-Porat (Proc. Nat. Acad. Sci., U.S.A. 66, 799–806, 1970).

The complete pseudorabies virus obtained from the PK-15 cells was inactivated at 60° C. for 4 hours. The complete inactivated pseudorabies virus or the EAG were used for immunization of mice against infection by pseudorabies virus.

The immunization of mice was carried out by modification of the method described by E. N. Kitces et al. (Infection and Immunity Vol. 16, 955–960, 1970). Complete, heat-inactivated virus particles or EAG (subunit vaccine) of HSV I or pseudorabies virus were injected intramuscularly into adult CF-1 mice. The degree of immunization was adjusted so that some of the animals survived a challenge infection with infectious virus which had a lethal course in the others.

The treatment with the said compounds can be carried out intraperitoneally, subcutaneously, intramuscularly or intravenously. This may entail the compounds being administered either separately or together with the vaccine.

The challenge infection with infectious virus was carried out intraperitoneally, intracerebrally or intranasally 7–13 days after the immunization. Dead animals were recorded each day. The observation period lasted 14 days since experience has shown that no animal dies from the infection after this period.

Differences in the survival rate and survival time of treated and untreated, immunized animals were determined. The results are shown in Tables 3–6.

The compounds according to the invention, of the formula I, thus exhibit a potent adjuvant action on administration of virus vaccines. Hence they can be used for human and animal virus infections which are amenable to immunoprophylaxis. The use of the said compounds is particularly indicated for vaccines which have only low immunogenicity, for example for subunit vaccines prepared by genetic engineering or by chemical means.

The indications which may be mentioned as examples for the compounds according to the invention are the following virus infections which are amenable to immunoprophylasis:

(a) In human medicine: infections with influenza, mumps, measles, rubella, hepatitis and herpes viruses (b) in veterinary medicine: infections with pseudorabies virus (cattle, pig), rhinopneumonitis virus (horse), and Marek virus (chicken), foot-and-mouth virus (cattle, pig) and bovine influenza.

This list is by way of example and should by no means be regarded as restrictive.

TABLE 3

Adjuvant action of substances according to the invention on administration of a *herpes simplex* virus vaccine

| | |
|---|---|
| Immunization: | intramuscular |
| Administration of substance: | intramuscular, together with antigen |
| Challenge infection: | intraperitoneal |

| Example No. | Survival rate in % (n = 10) | Mean survival rate (days) |
|---|---|---|
| M 66[(1)] | 100 | >14* |
| M 51 | 90 | 13.3* |
| M 74 | 80 | 12.8* |
| M 34 | 80 | 12.8* |
| untreated control | 30 | 9.3 |

[(1)]Dose: 10 mg/kg
*p = 0.05–0.01. The p values were determined by the t test.

TABLE 4

Adjuvant action of substance M 66 on administration of a *herpes simplex* virus vaccine

| | |
|---|---|
| Immunization: | intramuscular |
| Administration of substance: | intramuscular, together with antigen |
| Challenge infection: | intracerebral |

| Dose (mg/kg) | Survival rate in % (n = 10) | Mean survival rate (days) |
|---|---|---|
| 0 | 0 | 5.6 |
| 12.5 | 40 | 10.1* |
| 25 | 40 | 9.8* |

*p = 0.05–0.01. The p values were determined by the t test.

TABLE 5

Adjuvant action of substance M 66 on administration of a pseudorabies virus vaccine

| | |
|---|---|
| Immunization: | intramuscular |
| Administration of substance: | intramuscular, together with antigen |
| Challenge infection: | intraperitoneal |

| Dose (mg/kg) | Survival rate in % (n = 10) | Mean survival rate (days) |
|---|---|---|
| 0 | 60 | 10.5 |
| 1.5 | 90 | 13.1 |
| 3.0 | 100 | >14.0* |
| 6.0 | 100 | >14.0* |
| 12.0 | 100 | >14.0* |

*p = 0.05–0.025. The p values were determined by the t test.

TABLE 6

Adjuvant action of substance M 66 on administration of a *herpes simplex* subunit vaccine

| | |
|---|---|
| Immunization: | intramuscular (80 μg/mouse) |
| Administration of substance: | intramuscular, together with antigen |
| Challenge infection: | intranasal |

| Dose (mg/kg) | Survival rate in % (n = 10 mice) | Mean survival rate (days) |
|---|---|---|
| 0 | 50 | 10.6 |
| 6 | 100 | >14.0* |

*P = 0.01–0.005. The p values were determined by the t test.

In addition, the new compounds can also be used, without simultaneous dosage of antigen, to promote defense reactions, which are already taking place below the threshold level, in humans and animals. Accordingly, the compounds are particularly suitable for the stimulation of the body's own defenses, for example in the case of chronic and acute infections or of selective (antigen-specific) immunological deficits, and of inborn, as well as acquired, general (that is to say not antigen-specific) states of immunological deficit, such as occur in the elderly, during the course of serious primary disorders and, in particular, after treatment with ionizing radiation or with substances having an immunosuppressant action. Thus, the said substances can preferably also be administered combined with antiinfective antibiotics, chemotherapeutics or other methods of treatment in order to counteract damage to the macroorganism. Finally, the substances which have been described are also suitable for the general propylaxis of infectious diseases in humans and animals.

The compounds according to the invention increase the survival rate in the animal model of systemic mouse candidosis and of acute bacterial infection, and increase the body's own defenses against chronic persistent infections.

Description of the Experiments

Mice of the type SPF-CFW 1 were infected intravenously with $2-6\times10^5$ logarithmically growing cells of *Candida albicans* suspended in physiological saline solution. The first signs of disease were detectable in untreated control animals starting with the third day after infection. The first animals die of acute renal failure by the fifth day and, as a rule, more than 80% of the untreated animals have died by the 14th day after infection. The compounds according to the invention act in this test to retard the disease. A significant action retarding the disease was achieved with, for example, the compounds according to Example M 17, M 61 and M 66, when the substances were administered parenterally (i.p. or s.c.) 24 hours before the infection in concentrations of 1–50 mg/kg of body weight.

A statistically significant prolongation of the survival time of treated animals compared with the untreated controls was observed. About 50% of the treated animals survived an observation period of 14 days, compared with about 20% of untreated control animals.

The compounds according to the invention can be used by themselves as a propylactic, and for controlling existent infections, or in combination with antibiotic treatment to increase the therapeutic action of antibiotics and chemotherapeutics (for example penicillins, cephalosporins, aminoglycosides, etc.) in infected humans and animals.

It has been found that infections of the mouse with pathogenic organisms, which lead to the death of the experimental animals within 24–48 hours, can be treated by a prophylactic treatment—preferably intraperitoneal—with 1–80 mg/kg of the compounds according to the invention. This is true for a large number of Gram-positive (for example Staphylococci) and Gram-negative (for example E. coli, Klebsiella, Proteus, Pseudomonas) pathogens. This list is by way of example and should by no means be regarded as restrictive. Thus, for example, 40 to 100% of mice which have been infected with the pathogenic strain Klebsiella 63 survive this infection after treatment (for example 18 hours before the infection) with 10–40 mg/kg of the compounds according to the invention, of Examples M 4, M 5, M 34, M 92 and M 51, whereas only 0 to 30% of the untreated control animals survived.

It was possible to show in another experimental model that the therapeutic efficacy of antibiotics can be increased by the compounds according to the invention. Thus, mice were infected with the strain Pseudomonas W. This infection leads to the death of most of the control animals within 24 hours. Another group was treated with 4 mg/kg sisomicin 30 hours after the infection. It was possible to show that the therapeutic efficacy of the sisomicin could be crucially improved in the test group which had been treated with the compounds according to the invention (for examples see above) 18 hours before the infection.

The experimental animals used for the experiments on subacute infection were CFW$_1$ mice. The groups were treated with 0.1 mL in each case of the substances formulated in 3% ethanol, and with the control formulation (containing no substance) in the control groups, in each case three times i.m. The treatment was carried out 24 hours and one hour before the infection and 24 hours after infection. The i.p. infection with *Salmonella typhimurium* strain LT2 and about $5\times10^5$ organisms/mouse in 0.25 ml corresponded to one LD50. The course of the infection in the control group was manifested by a four-day initial phase of the infection in which the animals did not die. This initial phase of the infection offers the animals the opportunity to activate cellular immune mechanisms and thus stimulates the non-specific resistance to a latent or chronic infection. About 50% of the control animals died from day 4 to 12 following infection. The experiment was terminated after an observation period of 21 days.

The experiments were evaluated by comparison of the control groups with the treated groups. This entailed both the reduced mortality rate and the retardation of the start of the mortality phase being used as criterion for the efficacy of the substances.

The compounds M 1, M 92, M 17 and M 54 showed both a prolongation of the time before the animals started to die and a marked increase in the survival rate. The effects were observed in the concentration range 1 to 10 mg/kg of body weight.

Further experiments on inbred mice (CBA/J with normal resistance to infection (Ity$^r$) with *Salmonella typhimurium* show, after subcutaneous or intraperitoneal infection with $10^4-10^5$ colony-forming units, a chronic course of the disease with appearance of the organisms in the blood and colonization of the liver and spleen. The bacteria are detectable in the organs for 6–8 weeks, that is to say the infection has a chronic persistent course.

Mice were allocated at random to groups of five or ten animals, and were treated, for example with various doses of the substances M 52 and M 54 ($1\times$a day). A group of mice treated with solvent served as the control. On prophylactic administration (intraperitoneal or subcutaneous) of M 52 on days $-4$, $-3$, $-2$ and $-1$ before the inoculation of the pathogen, the organism counts in the liver 21 days after the infection were found to be reduced by 90% compared with the controls.

The substance M 54, for example administered intraperitoneally during the infection on days $+3$, $+4$, $+5$ and $+6$, likewise brought about a reduction of about 90% in the organism count in the liver on the seventh day after infection.

Untreated mice infected with salmonella show a suppression of the T-cell-mediated immunity from the second week after administration of pathogen, which is detectable by the reduced rate of incorporation of $^3$H-thymidine into the deoxyribonucleic acid of their spleen lymphocytes on exposure to the mitogens phytohaemagglutinin (PHA) and concanavalin A (Con A). Following prophylactic treatment of the animals with one of the substances according to the invention, for example M 52, the suppression of the T-cell-mediated immunity brought about by the infection was markedly less than in control animals. The ability of the spleen lymphocytes to be stimulated reached values which are observed in non-infected animals. These effects were observed at a dose of 5 mg/kg of body weight. Without infection, no increase in the proliferation of spleen lymphocytes was detected with M 52.

Although compounds of the type described display their potentiating action in the mouse following, for example, merely a single dose of 10 mg/kg i.p. or orally, no toxic effects are observed even of administration of 100 mg/kg. The said substances are thus well tolerated.

The pharmaceutical products of the present invention are preferably tablets or gelatine capsules which contain the active compounds together with diluents, for example lactose, dextrose, sucrose, mannitol, sorbitol or cellulose, and/or lubricants, for example diatomaceous earth, talc, stearic acid or salts thereof, such as magnesium or calcium stearate, and/or polyethylene glycol. Tablets likewise contain binders, for example magnesium aluminum silicate, starches, such as maize, wheat, rice or arrowroot starch, gelatin, tragacanth, methylcellulose, sodium carboxymethylcellulose and/or polyvinylpyrrolidone, and, if desired, disintegrants, for example starches, agar, alginic acid or a salt thereof, such as sodium alginate, and/or effervescent mixtures, or adsorbents, pigments, flavourings and sweeteners. Injectable products are preferably isotonic aqueous solutions or suspensions. Suppositories, ointments or creams are primarily fatty emulsions or suspensions. The pharmaceutical products can be sterilized and/or contain auxiliaries, for example preservatives, stabilizers, wetting agents and/or emulsifiers, solubilizers, salts to regulate the osmotic pressure and/or buffers. The present pharmaceutical products which, if desired, can contain further pharmacologically valuable substances, are produced in a manner known per se, for example by conventional mixing, granulating or coating processes, and contain from about 0.1% to about 75%, in particular from about 1% to 50%, of the said active compounds.

The products of the present invention which are administered orally can also be provided with a coating which is resistant to gastric juice.

The compounds according to the invention can be used as resistance-increasing and immunopotentiating agents for the treatment of chronic and acute infections (for example bacterial, viral and parasitic) and malignant tumors. They can likewise be used as adjuvants for vaccination, for the stimulation of phagocytosis, and for modulating the defense and immune systems.

The effect of long-term treatment on immunologically mediated processes using the model of adjuvant-induced arthritis.

In a 30-day experiment, the effect of substances of the present class of compounds was investigated in the model of adjuvant-induced arthritis of the rat (Pearson, C. M. and F. D. Wood, Arthr. Rheu. 2, 440 (1959)), a model of chronic inflammation with, according to the most recent communications, a pronounced cellular (T-lymphocyte) component.

On daily subcutaneous administration over a period of 20 days, the substances of the present compounds according to the invention markedly suppress the lesions on the paw (primary lesion) injected with complete Freund's adjuvant (CFA); the active substance M 66 may be mentioned as an example of the peptidoglycolipid analogues.

The systemization of the disease taking place after 10 days, measured by the unafflicted rat paw (secondary lesion), could be significantly suppressed by M 66, and was also restrained over a period of 10 days after discontinuation of the treatment.

Accordingly, the compounds exhibit properties which make them valuable for treatments of immunologically related processes associated with chronic inflammations (for example diseases of the rheumatic type) and immunological dysregulations (certain types of immunodeficiency).

EXAMPLES

A. General method for the preparation of N-(2-benzyloxycarbonylamino-2-deoxy-β-D-glucopyranosyl)-alkylamine IV A mixture of 10 mmol of 2-benzyloxycarbonylamino-2-deoxy-D-glucopyranose (II) (preparation: E. Chargaff and M. Borarnick, J. Biol. Chem. 118 (1937) 421) and 20 mmol of alkylamine III was dissolved in 60 ml of hot methanol, and the solution was stirred under reflux for 3 h. After cooling to room temperature, the solvent was removed in vacuo. The remaining residue was dissolved in 60 ml of dimethylformamide, and the solution was extracted five times with 20 ml of n-hexane each time. The DMF solution was used for the N-acylations without further manipulations.

The N-(2-benzyloxycarbonylamino-2-deoxy-β-D-galactopyranosyl)-alkylamines (IV) were also prepared by the same method.

B. General method for the preparation of N-(2-benzyloxycarbonylamino-2-deoxy-β-D-glucopyranosyl)-N-alkyl-carboxamides (VI) (X=—CH$_2$—)

11 mmol of carboxylic acid (V, R$^{11}$=—OH) were dissolved in 15 ml of absolute tetrahydrofuran and, after addition of 10.5 mmol of ethyl chloroformate and 10.5 mmol of triethylamine, the mixture was stirred at room temperature for 1 h. The ammonium salt which formed was filtered off with suction and washed twice with 3 ml of tetrahydrofuran each time. The combined filtrates were added to the solution of the glycosylamine (IV) prepared by process A. The combined solutions were stirred at room temperature for 4 h. The mixture was evaporated under high vacuum, and the resulting residue was purified by column chromatography (mobile phase dichloromethane/methanol=20:1).

Starting from the N-(2-benzyloxycarbonylamino-2-deoxy-β-D-galactopyranosyl)-alkylamines (IV), the corresponding N-(2-benzyloxycarbonylamino-2-deoxy-β-D-galactopyranosyl)-N-alkyl-carboxamides VI (X=CH$_2$) were prepared by the same methods.

C. General method for the preparation of the N-(3,4,6-tri-O-acetyl-2-benzyloxycarbonylamino-2-deoxy-β-D-glucopyranosyl)-N-alkyl-carboxamides IX (X=—CH$_2$—)

The N-(2-benzylcarbonylamino-2-deoxy-β-D-glucopyranosyl)-N-alkyl-carboxamides VI (X=CH$_2$), which were prepared by the general method B, were dissolved, without previous purification by chromatography, in 30 ml of pyridine and, after addition of 20 ml of acetic anhydride, heated at 50° C. for 30 min. After the mixture had been cooled to room temperature, it was evaporated in vacuo. The residue was taken up in toluene and evaporated several times. The residue was dissolved in 50 ml of dichloromethane, and the solution was filtered through 5 g of silica gel 60 (MERCK). The filtrate was evaporated in vacuo.

The residue was dissolved in hot methanol, and crystallized at room temperature. The resulting crystals were recrystallized from methanol.

The N-(3,4,6-tri-O-acetyl-2-benzyloxycarbonylamino-2-deoxy-β-D-galactopyranosyl)-N-alkyl-carboxamides IX (X=—CH$_2$—) were prepared analogously from the N-(2-benzyloxycarbonylamino-2-deoxy-β-D-galactopyranosyl)-N-alkyl-carboxamides VI (X=CH$_2$) by reaction with acetic anhydride and pyridine.

D. General method for the preparation of the N-(2-benzyloxycarbonylamino-2-deoxy-β-D-glucopyranosyl)-N-alkyl-carboxamides VI (X=—CH$_2$—) from the corresponding tri-O-acetates IX (X=—CH$_2$—)

10 mmol of the N-(3,4,6-tri-O-acetyl-2-benzyloxycarbonylamino-2-deoxy-β-D-glucopyranosyl)-N-alkyl-carboxamides IX (X=—CH$_2$—) were dissolved in 50 ml of absolute methanol, and 0.5 ml of 1N sodium methanolate was added. The mixture was heated at 50° C. for 30 min, then cooled to room temperature, and neutralized with Lewatit®SC 108 (H+ form) ion exchange resin. The ion exchange resin was filtered off, and the filtrate was evaporated to a syrup.

From the N-(3,4,6-tri-O-acetyl-2-benzyloxycarbonylamino-2-deoxy-β-D-galactopyranosyl)-N-alkyl-carboxamides IX (X=—CH$_2$—) were prepared analogously by transesterification the corresponding N-(2-benzyloxycarbonylamino-2-de-oxy-β-D-galactopyranosyl)-N-alkyl-carboxamides VI (X=—CH$_2$—).

E. General method for the preparation of the O-alkyl N-(2-benzyloxycarbonylamino-2-deoxy-β-D-glucopyranosyl)-N-alkyl-carbamates VI (X=O)

10 mmol of the N-(2-benzyloxycarbonylamino-2-deoxy-β-D-glucopyranosyl)-alkylamine IV, prepared by method A, were dissolved in 20 ml of absolute tetrahydrofuran, and 10 mmol of potassium carbonate were added.

While stirring, 10 mmol of alkyl chloroformate VII, dissolved in 10 ml of absolute tetrahydrofuran, were added dropwise. The mixture was stirred for up to 1 h, and then filtered, and the filtrate was evaporated in vacuo. The residue was purified by column chromatography: (mobile phase dichloromethane/methanol=10:1).

From the N-(2-benzyloxycarbonylamino-2-deoxy-β-D-galactopyranosyl)-alkylamines IV were prepared analogously the corresponding O-alkyl N-(2-benzyloxycarbonylamino-2-deoxy-β-D-galactopyranosyl)-N-alkyl-carbamates VI (X=O).

F. General method for the preparation of the N-(2-benzyloxycarbonylamino-2-deoxy-β-D-glucopyranosyl)-N-alkyl-N'-alkylureas VI (X=

10 mmol of the N-(2-benzyloxycarbonylamino-2-deoxy-β-D-glucopyranosyl)-alkylamine IV, prepared by method A, were dissolved in 20 ml of absolute tetrahydrofuran and 5 ml of methanol. While stirring this solution, a solution of 10 mmol of alkyl isocyanate VIII in 10 ml of tetrahydrofuran was added dropwise. The mixture was stirred at room temperature for 2 h and then evaporated in vacuo. The resulting syrup was purified by chromatography on silica gel. (Mobile phase dichloromethane/methanol=15:1).

From the N-(2-benzyloxycarbonylamino-2-deoxy-β-D-galactopyranosyl)-alkylamines IV were prepared analogously the corresponding N-(2-benzyloxycarbonylamino-2-deoxy-β-D-galactopyranosyl)-N-alkyl-N'-alkylureas VI (X=—NH—).

G. General method for the preparation of the N-(2-amino-2-deoxy-β-D-glucopyranosyl)-N-alkyl-carboxamides X (X=—CH$_2$—)

10 mmol of the N-(2-benzyloxycarbonylamino-2-deoxy-β-D-glucopyranosyl)-N-alkylcarboxamides VI (X= were dissolved in 20 ml of tetrahydrofuran, 20 ml of methanol and 4 ml of glacial acetic acid, and hydrogenated under atmospheric pressure in the presence of 500 mg of 10% palladium/charcoal. After uptake of hydrogen was complete, the catalyst was filtered off, and the filtrate was evaporated in vacuo. The resulting product was obtained as the acetic acid salt.

From the N-(2-benzyloxycarbonylamino-2-deoxy-β-D-galactopyranosyl)-N-alkyl-carboxamides VI (X=—CH$_2$—) were obtained analogously, by hydrogenation, the corresponding N-(2-amino-2-deoxy-β-D-galactopyranosyl)-N-alkylcarboxamides X (X=—CH$_2$—).

H. General method for the preparation of the O-alkyl N-(2-amino-2-deoxy-β-D-glucopyranosyl)-N-alkyl-carbamates X (X=—O—)

The hydrogenation of 10 mmol of O-alkyl N-(2-benzyloxycarbonylamino-2-deoxy-β-D-glucopyranosyl)-N-alkyl-carbamate VI (X=O) was carried out as described under G.

From the O-alkyl N-(2-benzyloxycarbonylamino-2-deoxy-β-D-galactopyranosyl)-N-alkyl-carbamates VI (X=—O—) were prepared analogously, by hydrogenation, the corresponding O-alkyl N-(2-amino-2-deoxy-β-D-galactopyranosyl)-N-alkyl-carbamates X (X=—O—).

I. General method for the preparation of the N-(2-amino-2-deoxy-β-D-glucopyranosyl)-N-alkyl-N'-alkylureas X (X=—NH—)

The hydrogenation of 10 mmol of N-(2-benzyloxycarbonylamino-2-deoxy-β-D-glucopyranosyl)-N-alkyl-N'-alkylurea VII (X=—NH—) was carried out as described under H.

From the N-(2-benzyloxycarbonylamino-2-deoxy-β-D-galactopyranosyl)-N-alkyl-N-'-alkylureas VI (X=—NH—) were prepared analogously the corresponding N-(2-amino-2-deoxy-β-D-galactopyranosyl)-N-alkyl-N'-alkylureas X (X=—NH—).

J. General method for the preparation of N-(2-(2-benzyloxycarbonylamino-acylamido)-2-deoxy-β-D-hexopyranosyl)-N-alkyl-carboxamides XII (X=—CH$_2$), O-alkyl carbamates XII (X=—O—) and N'-alkylureas XII (X=—NH—).

10.0 mmol of the N-benzyloxycarbonylamino acid XI were dissolved in 30 ml of absolute tetrahydrofuran, 12.5 mmol of N-hydroxysuccinimide were added, and the mixture was cooled to 0°. After addition of 10.0 mmol of dicyclohexylcarbodiimide, the mixture was stirred at 20° C. for 3 h and then at room temperature for 1 h. The precipitated urea was filtered off with suction, and the filtrate was added to a solution of 9.5 mmol of amino compound X in 50 ml of absolute tetrahydrofuran and 9.5 mmol of triethylamine at 0° C.

The mixture was slowly warmed to room temperature, and stirred at room temperature for 2 h. The mixture was evaporated in vacuo, and the syrupy residue was dissolved in 200 ml of dichloromethane and 40 ml of 2-propanol, and the solution was extracted several times with 60 ml of 5% strength aqueous sodium chloride solution each time.

The organic phase was dried over magnesium sulphate and evaporated in vacuo to a syrup. The syrup was separated by column chromatography on silica gel 60 (Mobile phase dichloromethane/methanol/aqueous ammonia=20:1/5:1).

K. General method for the preparation of the N-(3,4,6-tri-O-acetyl-2-(2-benzyloxycarbonylaminoacylamido)-2-deoxy-β-D-hexopyranosyl)-N-alkyl-carboxamides XV (X=—CH$_2$—), O-alkyl-carbamates XV (X=—O—) and -N'-alkylureas XV (X=—NH—)

The glycopyranosylamides, -carbamates and -ureas XII prepared by general method J were, before the chromatographic purification step described there, dissolved in 50 ml of pyridine and 30 ml of acetic anhydride, and the solution was heated at 40° for 1 h. 100 ml of ice-water were added to the mixture. The organic substance was extracted with 150 ml of dichloromethane, and then the dichloromethane phase was exhaustively extracted with 1N hydrochloric acid, then with saturated aqueous sodium bicarbonate and finally with water, and was dried over magnesium sulphate. The dichloromethane phase was evaporated, and the remaining syrup was dissolved in hot methanol.

The tri-O-acetates XV crystallized on cooling slowly to room temperature or to 10° C.

L. General method for the preparation of compounds XII by O-deacetylation of the tri-O-acetates XV:

10 mmol of the tri-O-acetyl-glycopyranosylamides XV (X=—CH$_2$—), -carbamates XV (X=—O—) or -ureas XV (X=—NH—) were dissolved in 20 ml of absolute tetrahydrofuran and 30 ml of absolute methanol, and after addition of 0.2 ml of 1 N sodium methanolate solution the solution was heated at 50° for 1 h. The working up of the reaction mixtures was carried out as described for method D.

M. General method for the preparation of the N-(2-(2-aminoacylamido)-2-deoxy-β-D-hexopyranosyl)-N-alkyl-carboxamides I (X=—CH$_2$—, R$^3$=R$^4$=R$^5$=—H), O-alkyl-carbamates I (X=—O—, R$^3$=R$^4$=R$^5$=—H) and N'-alkylureas I (X=—NH—, R$^3$=R$^4$=R$^5$=—H).

10 mmol of the N-(2-benzyloxycarbonylamino)acylamido-2-deoxy-β-D-hexopyranosyl)-N-alkyl-carboxamides XII (X=—CH$_2$—), O-alkyl-carbamates XII (X=—O—) or —N'-alkylureas XII (X=—NH—) were dissolved in 50 ml of tetrahydrofuran, 50 ml of methanol and 10 ml of glacial acetic acid, and hydrogenation was carried out under atmospheric pressure in the presence of 1.0 g of 10% palladium/charcoal. The mixtures were worked up as for method G.

The following compounds of the general structure IV can be prepared by the method detailed under A:

A.1 N-(2-benzyloxycarbonylamino-2-deoxy-β-D-glucopyranosyl)-octylamine
A.2 N-(2-benzyloxycarbonylamino-2-deoxy-β-D-glucopyranosyl)-decylamine
A.3 N-(2-benzyloxycarbonylamino-2-deoxy-β-D-glucopyranosyl)-dodecylamine
A.4 N-(2-benzyloxycarbonylamino-2-deoxy-β-D-glucopyranosyl)-tetradecylamine
A.5 N-(2-benzyloxycarbonylamino-2-deoxy-β-D-glucopyranosyl)-hexadecylamine
A.6 N-(2-benzyloxycarbonylamino-2-deoxy-β-D-glucopyranosyl)-octadecylamine
A.7 N-(2-benzyloxycarbonylamino-2-deoxy-β-D-glucopyranosyl)-eicosylamine
A.8 N-(2-benzyloxycarbonylamino-2-deoxy-β-D-galactopyranosyl)-decylamine
A.9 N-(2-benzyloxycarbonylamino-2-deoxy-β-D-galactopyranosyl)-dodecylamine
A.10 N-(2-benzyloxycarbonylamino-2-deoxy-β-D-galactopyranosyl)-tetradecylamine
A.11 N-(2-benzyloxycarbonylamino-2-deoxy-β-D-galactopyranosyl)-hexadecylamine
A.12 N-(2-benzyloxycarbonylamino-2-deoxy-β-D-galactopyranosyl)-octadecylamine The following compounds of the general structure VI (X=—CH$_2$—) can be obtained by the method detailed under B.

B.1 N-(2-benzyloxycarbonylamino-2-deoxy-β-D-glucopyranosyl)-N-octyl-tetradecanoamide
B.2 N-(2-benzyloxycarbonylamino-2-deoxy-β-D-glucopyranosyl)-N-octyl-octadecanoamide
B.3 N-(2-benzyloxycarbonylamino-2-deoxy-β-D-glucopyranosyl)-N-decyl-dodecanoamide
B.4 N-(2-benzyloxycarbonylamino-2-deoxy-β-D-glucopyranosyl)-N-decyl-tetradecanoamide
B.5 N-(2-benzyloxycarbonylamino-2-deoxy-β-D-glucopyranosyl)-N-decyl-octadecanoamide
B.6 N-(2-benzyloxycarbonylamino-2-deoxy-β-D-glucopyranosyl)-N-dodecyl-dodecanoamide
B.7 N-(2-benzyloxycarbonylamino-2-deoxy-β-D-glucopyranosyl)-N-dodecyl-tetradecanoamide
B.8 N-(2-benzyloxycarbonylamino-2-deoxy-β-D-glucopyranosyl)-N-dodecyl-hexadecanoamide
B.9 N-(2-benzyloxycarbonylamino-2-deoxy-β-D-glucopyranosyl)-N-dodecyl-octadecanoamide
B.10 N-(2-benzyloxycarbonylamino-2-deoxy-β-D-glucopyranosyl)-N-tetradecyl-dodecanoamide
B.11 N-(2-benzyloxycarbonylamino-2-deoxy-β-D-glucopyranosyl)-N-tetradecyl-tetradecanoamide
B.12 N-(2-benzyloxycarbonylamino-2-deoxy-β-D-glucopyranosyl)-N-tetradecyl-hexadecanoamide
B.13 N-(2-benzyloxycarbonylamino-2-deoxy-β-D-glucopyranosyl)-N-tetradecyl-octadecanoamide
B.14 N-(2-benzyloxycarbonylamino-2-deoxy-β-D-glucopyranosyl)-N-tetradecyl-eicosanoamide
B.15 N-(2-benzyloxycarbonylamino-2-deoxy-β-D-glucopyranosyl)-N-hexadecyl-decanoamide
B.16 N-(2-benzyloxycarbonylamino-2-deoxy-β-D-glucopyranosyl)-N-hexadecyl-dodecanoamide
B.17 N-(2-benzyloxycarbonylamino-2-deoxy-β-D-glucopyranosyl)-N-hexadecyl-tetradecanoamide
B.18 N-(2-benzyloxycarbonylamino-2-deoxy-β-D-glucopyranosyl)-N-hexadecyl-hexadecanoamide
B.19 N-(2-benzyloxycarbonylamino-2-deoxy-β-D-glucopyranosyl)-N-hexadecyl-octadecanoamide
B.20 N-(2-benzyloxycarbonylamino-2-deoxy-β-D-glucopyranosyl)-N-octadecyl-dodecanoamide
B.21 N-(2-benzyloxycarbonylamino-2-deoxy-β-D-glucopyranosyl)-N-octadecyl-tetradecanoamide
B.22 N-(2-benzyloxycarbonylamino-2-deoxy-β-D-glucopyranosyl)-N-octadecyl-hexadecanoamide
B.23 N-(2-benzyloxycarbonylamino-2-deoxy-β-D-glucopyranosyl)-N-octadecyl-octadecanoamide
B.24 N-(2-benzyloxycarbonylamino-2-deoxy-β-D-glucopyranosyl)-N-octadecyl-eicosanoamide B.25 N-(2-benzyloxycarbonylamino-2-deoxy-β-D-galactopyranosyl)-N-dodecyl-dodecanoamide B.26 N-(2-benzyloxycarbonylamino-2-deoxy-β-D-galactopyranosyl)-N-dodecyl-tetradecanoamide B.27 N-(2-benzyloxycarbonylamino-2-deoxy-β-D-galactopyranosyl)-N-dodecyl-octadecanoamide B.28 N-(2-benzyloxycarbonylamino-2-deoxy-β-D-galactopyranosyl)-N-tetradecyl-dodecanoamide B.29 N-(2-benzyloxycarbonylamino-2-deoxy-β-D-galactopyranosyl)-N-tetradecyl-tetradecanoamide B.30 N-(2-benzyloxycarbonylamino-2-deoxy-β-D-galactopyranosyl)-N-tetradecyl-octadecanoamide B.31 N-(2-benzyloxycarbonylamino-2-deoxy-β-D-galactopyranosyl)-N-octadecyl-dodecanoamide B.32 N-(2-benzyloxycarbonylamino-2-deoxy-β-D-galactopyranosyl)-N-octadecyl-tetradecanoamide B.33 N-(2-benzyloxycarbonylamino-2-deoxy-β-D-galactopyranosyl)-N-octadecyl-octadecanoamide The following compounds of the general structure IX (X=—CH$_2$—) can be obtained by the method detailed under C.

C.1 N-(3,4,6-tri-O-acetyl-2-benzyloxycarbonylamino-2-deoxy-β-D-glucopyranosyl)-N-dodecyl-dodecanoamide C.2 N-(3,4,6-tri-O-acetyl-2-benzyloxycarbonylamino-2-deoxy-β-D-glucopyranosyl)-N-dodecyl-tetradecanoamide C.3 N-(3,4,6-tri-O-acetyl-2-benzyloxycarbonylamino-2-deoxy-β-D-glucopyranosyl)-N-dodecyl-octadecanoamide C.4 N-(3,4,6-tri-O-acetyl-2-benzyloxycarbonylamino-2-deoxy-β-D-glucopyranosyl)-N-tetradecyl-dodecanoamide C.5 N-(3,4,6-tri-O-acetyl)-2-benzyloxycarbonylamino-2-deoxy-β-D-glucopyranosyl)-N-tetradecyl-tetradecanoamide C.6 N-(3,4,6-tri-O-acetyl-2-benzyloxycarbonylamino-2-deoxy-β-D-glucopyranosyl)-N-tetradecyl-octadecanoamide C.7 N-(3,4,6-tri-O-acetyl-2-benzyloxycarbonylamino-2-deoxy-β-D-glucopyranosyl)-N-octadecyl-dodecanoamide C.8 N-(3,4,6-tri-O-acetyl-2-benzyloxycarbonylamino-2-deoxy-β-D-glucopyranosyl)-N-octadecyl-tetradecanoamide C.9 N-(3,4,6-tri-O-acetyl-2-benzyloxycarbonylamino-2-deoxy-β-D-glucopyranosyl)-N-octadecyl-octadecanoamide C.10 N-(3,4-6-tri-O-acetyl-2-benzyloxycarbonylamino-2-deoxy-β-D-galactopyranosyl)-N-dodecyl-octadecanoamide C.11 N-(3,4,6-tri-O-acetyl-2-benzyloxycarbonylamino-2-deoxy-β-D-galactopyranosyl)-N-octadecyl-dodecanoamide C.12 N-(3,4,6-tri-O-acetyl-2-benzyloxycarbonylamino-2-deoxy-β-D-galactopyranosyl)-N-octadecyl-tetradecanoamide C.13 N-(3,4,6-tri-O-acetyl-2-benzyloxycarbonylamino-2-deoxy-62 -D-galactopyranosyl)-N-octadecyl-octadecanoamide

The following compounds of the general structure VI (X=—O—) can be obtained by the method detailed under E.

E.1 O-dodecyl N-(2-benzyloxycarbonylamino-2-deoxy-β-D-glucopyranosyl)-N-dodecyl-carbamate E.2 O-tetradecyl N-(2-benzyloxycarbonylamino-2-deoxy-β-D-glucopyranosyl)-N-dodecyl-carbamate E.3 O-octadecyl N-(2-benzyloxycarbonylamino-2-deoxy-β-D-glucopyranosyl)-N-dodecyl-carbamate E.4 O-dodecyl N-(2-benzyloxycarbonylamino-2-deoxy-β-D-glucopyranosyl)-N-tetracecyl-carbamate E.5 O-octadecyl N-(2-benzyloxycarbonylamino-2-deoxy-β-D-glucopyranosyl)-N-tetradecyl-carbamate E.6 O-dodecyl N-(2-benzyloxycarbonylamino-2-deoxy-β-D-glucopyranosyl)-N-octadecyl-carbamate E.7 O-tetradecyl N-(2-benzyloxycarbonylamihno-2-deoxy-β-D-glucopyranosyl)-N-octadecyl-carbamate E.8 octadecyl N-(2-benzyloxycarbonylamino-2-deoxy-β-D-glucopyranosyl)-N-octadecyl-carbamate E.9 O-dodecyl N-(2-benzyloxycarbonylamino-2-deoxy-β-D-galactopyranosyl)-N-dodecyl-carbamate E.10 O-tetradecyl N-(2-benzyloxycarbonylamino-2-deoxy-β-D-galactopyranosyl)-N-dodecyl-carbamate E.11 O-octadecyl N-(2-benzyloxycarbonylamino-2-deoxy-β-D-galactopyranosyl)-N-dodecyl-carbamate E.12 O-dodecyl N-(2-benzyloxycarbonylamino-2-deoxy-β-D-galactopyranosyl)-N-tetradecyl-carbamate E.13 O-tetradecyl N-(2-benzyloxycarbonylamino-2-deoxy-β-D-galactopyranosyl)-N-tetradecyl-carbamate E.14 O-hexadecyl N-(2-benzyloxycarbonylamino-2-deoxy-β-D-galactopyranosyl)-N-tetradecyl-carbamate E.15 O-octadecyl N-(2-benzyloxycarbonylamino-2-deoxy-β-D-galactopyranosyl)-N-tetradecyl-carbamate E.16 O-dodecyl N-(2-benzyloxycarbonylamino-2-deoxy-β-D-galactopyranosyl)-N-octadecyl-carbamate E.17 O-tetradecyl N-(2-benzyloxycarbonylamino-2-deoxy-β-D-galactopyranosyl)-N-octadecyl-carbamate E.18 O-octadecyl N-(2-benzyloxycarbonylamino-2-deoxy-β-D-galactopyranosyl)-N-octadecyl-carbamate The following compounds of the general structure VI (X=—NH—) can be obtained by the method detailed under F.

F.1 N-(2-benzyloxycarbonylamino-2-deoxy-β-D-glucopyranosyl)-N-dodecyl-N'-dodecyl-urea F.2 N-(2-benzyloxycarbonylamino-2-deoxy-β-D-glucopyranosyl)-N-dodecyl-N'-tetradecyl-urea F.3 N-(2-benzyloxycarbonylamino-2-deoxy-β-D-glucopyranosyl)-N-dodecyl-N'-octadecyl-urea F.4 N-(2-benzyloxycarbonylamino-2-deoxy-β-D-glucopyranosyl)-N-tetradecyl-N'-dodecyl-urea F.5 N-(2-benzyloxycarbonylamino-2-deoxy-β-D-glucopyranosyl)-N-tetradecyl-N'-octadcyl-urea F.6 N-(2-benzyloxycarbonylamino-2-deoxy-β-D-glucopyranosyl)-N-octadecyl-N'-dodecyl-urea F.7 N-(2-benzyloxycarbonylamino-2-deoxy-β-D-glucopyranosyl)-N-octadecyl-N'-tetradecyl-urea F.8 N-(2-benzyloxycarbonylamino-2-deoxy-β-D-glucopyranosyl)-N-octadecyl-N'-octadecyl-urea F.9 N-(2-benzyloxycarbonylamino-2-deoxy-β-D-galactopyranosyl)-N-dodecyl-N'-dodecyl-urea F.10 N-(2-benzyloxycarbonylamino-2-deoxy-β-D-galactopyranosyl)-N-dodecyl-N'-tetradecyl-urea F.11 N-(2-benzyloxycarbonylamino-2-deoxy-β-D-galactopyranosyl)-N-dodecyl-N'-octadecyl-urea F.12 N-(2-benzyloxycarbonylamino-2-deoxy-β-D-galactopyranosyl)-N-tetradecyl-N'-dodecyl-urea F.13 N-(2-benzyloxycarbonylamino-2-deoxy-β-D-galactopyranosyl)-N-tetradecyl-N'-tetradecyl-urea F.14 N-(2-benzyloxycarbonylamino-2-deoxy-β-D-galactopyranosyl)-N-tetradecyl-N'-octadecyl-urea F.15 N-(2-benzyloxycarbonylamino-2-deoxy-β-D-galactopyranosyl)-N-octadecyl-N'-dodecyl-urea F.16 N-(2-benzyloxycarbonylamino-2-deoxy-β-D-galactopyranosyl)-N-octadecyl-N'-tetradecyl-urea F.17 N-(2-benzyloxycarbonylamino-2-deoxy-β-D-galactopyranosyl)-N-octadecyl-N'-octadecyl-urea The following compounds of the general structure X (X=—CH$_2$—) can be obtained in the form of their acetic acid salts by the method detailed under G.

G.1 N-(2-amino-2-deoxy-β-D-glucopyranosyl)-N-dodecyl-dodecanoamide

G.2 N-(2-amino-2-deoxy-β-D-glucopyranosyl)-N-dodecyl-tetradecanoamide

G.3 N-(2-amino-2-deoxy-β-D-glucopyranosyl)-N-dodecyl-hexadecanoamide

G.4 N-(2-amino-2-deoxy-β-D-glucopyranosyl)-N-dodecyl-octadecanoamide

G.5 N-(2-amino-2-deoxy-β-D-glucopyranosyl)-N-tetradecyldodecanoamide

G.6 N-(2-amino-2-deoxy-β-D-glucopyranosyl)-N-tetradecyl-tetradecanoamide

G.7 N-(2-amino-2-deoxy-β-D-glucopyranosyl)-N-tetradecyl-hexadecanoamide

G.8 N-(2-amino-2-deoxy-β-D-glucopyranosyl)-N-tetradecyl-octadecanoamide

G.9 N-(2-amino-2-deoxy-β-D-glucopyranosyl)-N-hexadecyl-dodecanoamide

G.10 N-(2-amino-2-deoxy-β-D-glucopyranosyl)-N-hexadecyl-tetradecanoamide

G.11 N-(2-amino-2-deoxy-β-D-glucopyranosyl)-N-hexadecyl-hexadecanoamide

G.12 N-(2-amino-2-deoxy-β-D-glucopyranosyl)-N-hexadecyl-octadecanoamide

G.13 N-(2-amino-2-deoxy-β-D-glucopyranosyl)-N-octadecyl-dodecanoamide

G.14 N-(2-amino-2-deoxy-β-D-glucopyranosyl)-N-octadecyl-tetradecanoamide

G.15 N-(2-amino-2-deoxy-β-D-glucopyranosyl)-N-octadecyl-hexadecanoamide

G.16 N-(2-amino-2-deoxy-β-D-glucopyranosyl)-N-octadecyl-octadecanoamide

G.17 N-(2-amino-2-deoxy-β-D-galactopyranosyl)-N-dodecyl-dodecanoamide

G.18 N-(2-amino-2-deoxy-β-D-galactopyranosyl)-N-dodecyl-tetradecanoamide

G.19 N-(2-amino-2-deoxy-β-D-galactopyranosyl)-N-dodecyl-octadecanoamide

G.20 N-(2-amino-2-deoxy-β-D-galactopyranosyl)-N-tetradecyl-dodecanoamide

G.21 N-(2-amino-2-deoxy-β-D-galactopyranosyl)-N-tetradecyl-octadecanoamide

G.22 N-(2-amino-2-deoxy-β-D-galactopyranosyl)-N-octadecyl-dodecanoamide

G.23 N-(2-amino-2-deoxy-β-D-galalctopyranosyl)-N-octadecyl-tetradecanoamide

G.24 N-(2-amino-2-deoxy-β-D-galtactopyranosyl)-N-octadecyl-octadecanoamide

The following compounds of the general structure X (X=—O—) can be obtained in the form of their acetic acid salts by the method detailed under H.

H.1 O-dodecyl N-(2-amino-2-deoxy-β-D-glucopyranosyl)-N-dodecyl-carbamate

H.2 O-tetradecyl N-(2-amino-2-deoxy-β-D-glucopyranosyl)-N-dodecyl-carbamate

H.3 O-octadecyl N-(2-amino-2-deoxy-β-D-glucopyranosyl)-N-dodecyl-carbamate

H.4 O-dodecyl N-(2-amino-2-deoxy-β-D-glucopyranosyl)-N-tetradecyl-carbamate

H.5 O-octadecyl N-(2-amino-2-deoxy-β-D-glucopyranosyl)-N-tetradecyl-carbamate

H.6 O-dodecyl N-(2-amino-2-deoxy-β-D-glucopyranosyl)-N-octadecyl-carbamate

H.7 O-tetradecyl N-(2-amino-2-deoxy-β-D-glucopyranosyl)-N-octadecyl-carbamate

H.8 O-octadecyl N-(2-amino-2-deoxy-β-D-glucopyranosyl)-N-octadecyl-carbamate

H.9 O-dodecyl N-(2-amino-2-deoxy-β-D-galactopyranosyl)-N-dodecyl-carbamate

H.10 O-tetradecyl N-(2-amino-2-deoxy-β-D-galactopyranosyl)-N-dodecyl-carbamate

H.11 O-octadecyl N-(2-amino-2-deoxy-β-D-galatopyranosyl)-N-dodecyl-carbamate

H.12 O-dodecyl N-(2-amino-2-dexoy-β-D-galactopyranosyl )-N-tetradedecyl-carbamate H.13 O-octadecyl N-(2-amino-2-deoxy-β-D-galactopyranosyl)-N-tetradecyl-carbamate H.14 O-dodecyl N-(2-amino-2-deoxy-β-D-galactopyranosyl)-N-octadecyl-carbamate H.15 O-tetradecyl N-(2-amino-2-deoxy-β-D-galactopyranosyl)-N-octadecyl-carbamate H.16 O-octadecyl N-(2-amino-2-deoxy-β-D-galactopyranosyl)-N-octadecyl-carbamate The following compounds of the general structure X (X=—NH—) can be obtained in the form of their acetic acid salts by the method detailed under I.

I.1 N-(2-amino-2-deoxy-β-D-glucopyranosyl)-N-dodecyl-N'-dodecyl-urea

I.2 N-(2-amino-2-deoxy-β-D-glucopyranosyl)-N-dodecyl-N'-tetradecyl-urea

I.3 N-(2-amino-2-deoxy-β-D-glucopyranosyl)-N-dodecyl-N'-octadecyl-urea

I.4 N-(2-amino-2-deoxy-β-D-glucopyranosyl)-N-tetradecyl-N'-dodecyl-urea

I.5 N-(2-amino-2-deoxy-β-D-glucopyranosyl)-N-tetradecyl-N'-octadecyl-urea

I.6 N-(2-amino-2-deoxy-β-D-glucopyranosyl)-N-octadecyl-N'-dodecyl-urea

I.7 N-(2-amino-2-deoxy-β-D-glucopyranosyl)-N-octadecyl-N'-tetradecyl-urea

I.8 N-(2-amino-2-deoxy-β-D-glucopyranosyl)-N-octadecyl-N'octadecyl-urea

I.9 N-(2-amino-2-deoxy-β-D-galactopyranosyl)-N-dodecyl-N'-dodecyl-urea

I.10 N-(2-amino-2-deoxy-β-D-galactopyranosyl)-N-dodecyl-N'-tetradecyl-urea

I.11 N-(2-amino-2-deoxy-β-D-galactopyranosyl)-N-dodecyl-N'-octadecyl-urea

I.12 N-(2-amino-2-deoxy-β-D-galactopyranosyl)-N-tetradecyl-N'-dodecyl-urea

I.13 N-(2-amino-2-deoxy-β-D-galactopyranosyl)-N-tetradecyl-N'-octadecyl-urea

I.14 N-(2-amino-2-deoxy-β-D-galactopyranosyl)-N-octadecyl-N'-dodecyl-urea

I.15 N-(2-amino-2-deoxy-β-D-galactopyranosyl)-N-octadecyl-N'-tetradecyl-urea

I.16 N-(2-amino-2-deoxy-β-D-galactopyranosyl)-N-octadecyl-N'-octadecyl-urea

The following compounds of the general structure XII (X=—CH$_2$—) can be obtained by the method detailed under J.

J.1 N-(2-(N-benzyloxycarbonyl-glycinamido)-2-deoxy-β-D-glucopyranosyl)-N-dodecyl-dodecanoamide J.2 N-(2-(N-benzyloxycarbonyl-glycinamido)-2-deoxy-β-D-glucopyranosyl)-N-dodecyl-tetradecanoamide J.3 N-(2-(N-benzyloxycarbonyl-glycinamido)-2-deoxy-β-D-glucopyranosyl)-N-dodecyl-hexadecanoamide J.4 N-(2-(N-benzyloxycarbonyl-glycinamido)-2-deoxy-β-D-glucopyranosyl)-N-dodecyl-octadecanoamide J.5 N-(2-(N-benzyloxycarbonyl-glycinamido)-2-deoxy-β-D-glucopyranosyl)-N-tetradecyl-dodecanoamide J.6 N-(2-(N-benzyloxycarbonyl-glycinamido)-2-deoxy-β-D-glucopyranosyl)-N-tetradecyl-tetradecanoamide J.7 N-(2-(N-benzyloxycarbonyl-glycinamido)-2-deoxy-β-D-glucopyranosyl)-N-tetradecyl-hexadecanoamide J.8 N-(2-(N-benzyloxycarbonyl-glycinamido)-2-deoxy-β-D-glucopyranosyl)-N-tetradecyl-octadecanoamide J.9 N-(2-(N-benzyloxycarbonyl-glycinamido)-2-deoxy-β-D-glucopyranosyl)-N-hexadecyl-dodecanoamide J.10 N-(2-(N-benzyloxycarbonyl-glycinamido)-2-deoxy-β-D-glucopyranosyl)-hexadecyl-tetradecanoamide J.11 N-(2-(N-benzyloxycarbonyl-glycinamido)-2-deoxy-β-D-glucopyranosyl)-N-hexadecyl-hexadecanoamide J.12 N-(2-(N-benzyloxycarbonyl-glycinamido)-2-deoxy-β-D-glucopyranosyl)-N-hexadecyl-octadecanoamide J.13 N-(2-(N-benzyloxycarbonyl-glycinamido)-2-deoxy-β-D-glucopyranosyl)-N-octadecyl-dodecanoamide J.14 N-(2-(N-benzyloxycarbonyl-glycinamido)-2-deoxy-β-D-glucopyranosyl)-N-octadecyl-tetradecanoamide J.15 N-(2-(N-benzyloxycarbonyl-glycinamido)-2-deoxy-β-D-glucopyranosyl)-N-octadecyl-hexadecanoamide J.16 N-(2-(N-benzyloxycarbonyl-glycinamido)-2-deoxy-β-D-glucopyranosyl)-N-octadecyl-octadecanoamide J.17 N-(2-(N-benzyloxycarbonyl-L-alaninamido)-2-deoxy-β-D-glucopyranosyl)-N-dodecyl-dodecanoamide J.18 N-(2-(N-benzyloxycarbonyl-L-alaninamido)-2-deoxy-β-D-glucopyranosyl)-N-dodecyl-tetradecanoamide J.19 N-(2-(N-benzyloxycarbonyl-L-alaninamido)-2-deoxy-β-D-glucopyranosyl)-N-dodecyl-hexadecanoamide J.20 N-(2-(N-benzyloxycarbonyl-L-alaninamido)-2-deoxy-β-D-glucopyranosyl)-N-dodecyl-octadecanoamide J.21 N-(2-(N-benzyloxycarbonyl-L-alaninamido)-2-deoxy-β-D-glucopyranosyl)-N-tetradecyl-dodecanoamide J.22 N-(2-(N-benzyloxycarbonyl-L-alaninamido)-2-deoxy β-D-glucopyranosyl)-N-tetradecyl-tetradecanoamide J.23 N-(2-(N-benzyloxycarbonyl-L-alaninamido)-2-deoxy-β-D-glucopyranosyl)-N-tetradecyl-hexadecanoamide J.24 N-(2-(N-benzyloxycarbonyl-L-alaninamido)-2-deoxy-β-D-glucopyranosyl)-N-tetradecyl-octadecanoamide J.25 N-(2-(N-benzyloxycarbonyl-L-alaninamido)-2-deoxy-β-D-glucopyranosyl)-N-hexadecyl-dodecanoamide J.26 N-(2-(N-benzyloxycarbonyl-L-alaninamido)-2-deoxy-β-D-glucopyranosyl)-N-hexadecyl-tetradecanoamide J.27 N-(2-(N-benzyloxycarbonyl-L-alaninamido)-2-deoxy-β-D-glucopyranosyl)-N-hexadecyl-hexadecanoamide J.28 N-(2-(N-benzyloxycarbonyl-L-alaninamido)-2-deoxy-β-D-glucopyranosyl)-N-hexadecyl-octadecanoamide J.29 N-(2-(N-benzyloxycarbonyl-L-alaninamido)-2-deoxy-β-D-glucopyranosyl)-N-octadecyl-dodecanoamide J.30 N-(2-(N-benzyloxycarbonyl-L-alaninamido)-2-deoxy-β-D-glucopyranosyl)-N-octadecyl-tetradecanoamide J.31 N-(2-(N-benzyloxycarbonyl-L-alaninamido)-2-deoxy-β-D-glucopyranosyl)-N-octadecyl-hexadecanoamide J.32 N-(2-(N-benzyloxycarbonyl-L-alaninamido)-2-deoxy-β-D-glucopyranosyl)-N-octadecyl-octadecanoamide J.33 N-(2-(N-benzyloxycarbonyl-D-alaninamido)-2-deoxy-β-D-glucopyranosyl)-N-dodecyl-dodecanoamide J.34 N-(2-(N-benzyloxycarbonyl-D-alaninamido)-2-deoxy-β-D-glucopyranosyl)-N-dodecyl-octadecanoamide J.35 N-(2-(N-benzyloxycarbonyl-D-alaninamido)-2-deoxy-β-D-glucopyranosyl)-N-tetradecyl-dodecanoamide J.36 N-(2-(N-benzyloxycarbonyl-D-alaninamido)-2-deoxy-β-D-glucopyranosyl)-N-tetradecyl-octadecanoamide J.37 N-(2-(N-benzyloxycarbonyl-D-alaninamido)-2-deoxy-β-D-glucopyranosyl)-N-octadecyl-dodecanoamide J.38 N-(2-(N-benzyloxycarbonyl-D-alaninamido)-2-deoxy-β-D-glucopyranosyl)-N-octadecyl-tetradecanoamide J.39 N-(2-(N-benzyloxycarbonyl-D-alaninamido)-2-deoxy-β-D-glucopyranosyl)-N-octadecyl-octadecanoamide J.40 N-(2-(N-benzyloxycarbonyl-L-phenylalaninamido)-2-deoxy-β-D-glucopyranosyl)-N-dodecyl-dodecanoamide J.41 N-(2-(N-benzyloxycarbonyl-L-phenylalaninamido)-2-deoxy-β-D-glucopyranosyl)-N-dodecyl-octadecanoamide J.42 N-(2-(N-benzyloxycarbonyl-L-phenylalaninamido)-2-deoxy-β-D-glucopyranosyl)-N-tetradecyl-dodecanoamide J.43 N-(2-(N-benzyloxycarbonyl-L-phenylalaninamido)-2-deoxy-β-D-glucopyranosyl)-N-tetradecyl-octadecanoamide J.44 N-(2-(N-benzyloxycarbonyl-L-phenylalaninamido)-2-deoxy-β-D-glycopyranosyl)-N-octadecyl-dodecanoamide J.45 N-(2-(N-benzyloxycarbonyl-L-phenylalaninamido)-2-deoxy-β-D-glucopyranosyl)-N-octadecyl-tetradecanoamide J.46 N-(2-(N-benzyloxycarbonyl-L-phenylalaninamido)-2-deoxy-β-D-glucopyranosyl)-N-octadecyl-octadecanoamide J.47 N-(2-(N-benzyloxycarbonyl-L-valinamido)-2-deoxy-β-D-glucopyranosyl)-N-dodecyl-dodecanoamide J.48 N-(2-(N-benzyloxycarbonyl-L-valinamido)-2-deoxy-β-D-glucopyranosyl)-N-dodecyl-octadecanoamide J.49 N-(2-(N-benzyloxycarbonyl-L-valinamido)-2-deoxy-β-D-glucopyranosyl)-N-tetradecyl-dodecanoamide J.50 N-(2-(N-benzyloxycarbonyl-L-valinamido)-2-deoxy-β-D-glucopyranosyl)-N-tetradecyl-octadecanoamide J.51 N-(2-(N-benzyloxycarbonyl-L-valinamido)-2-deoxy-β-D-glucopyranosyl)-N-octadecyl-dodecanoamide J.52 N-(2-(N-benzyloxycarbonyl-L-valinamido)-2-deoxy-β-D-glucopyranosyl)-N-octadecyl-tetradecanoamide J.53 N-(2-(N-benzyloxycarbonyl-L-valinamido)-2-deoxy-β-D-glucopyranosyl)-N-octadecyl-octadecanoamide J.54 N-(2-(N-benzyloxycarbonyl-L-leucinamido)-2-deoxy-β-D-glucopyranosyl)-N-dodecyl-dodecanoamide J.55 N-(2-(N-benzyloxycarbonyl-L-leucinamido)-2-deoxy-β-D-glucopyranosyl)-N-dodecyl-tetradecanoamide J.56 N-(2-(N-benzyloxycarbonyl-L-leucinamido)-2-deoxy-β-D-glucopyranosyl)-N-dodecyl-hexadecanoamide J.57 N-(2-(N-benzyloxycarbonyl-L-leucinamido)-2-deoxy-β-D-glucopyranosyl)-N-dodecyl-octadecanoamide J.58 N-(2-(N-benzyloxycarbonyl-L-leucinamido)-2-deoxy-β-D-glucopyranosyl)-N-tetradecyl-dodecanoamide J.59 N-(2-(N-benzyloxycarbonyl-L-leucinamido)-2-deoxy-β-D-glucopyranosyl)-N-tetradecyl-tetradecanoamide J.60 N-(2-(N-benzyloxycarbonyl-L-leucinamido)-2-deoxy-β-D-glucopyranosyl)-N-tetradecyl-hexadecanoamide J.61 N-(2-(N-benzyloxycarbonyl-L-leucinamido)-2-deoxy-β-D-glucopyranosyl)-N-tetradecyl-octadecanoamide J.62 N-(2-(N-benzyloxycarbonyl-L-leucinamido)-2-deoxy-β-D-glucopyranosyl)-N-hexadecyl-dodecanoamide J.63 N-(2-(N-benzyloxycarbonyl-L-leucinamido)-2-deoxy-β-D-glucopyranosyl)-N-hexadecyl-tetradecanoamide J.64 N-(2-(N-benzyloxycarbonyl-L-leucinamido)-2-deoxy-β-D-glucopyranosyl)-N-hexadecyl-hexadecanoamide J.65 N-(2-(N-benzyloxycarbonyl-L-leucinamido)-2-deoxy-β-D-glucopyranosyl)-N-hexadecyl-octadecanoamide J.66 N-(2-(N-benzyloxycarbonyl-L-leucinamido)-2-deoxy-β-D-glucopyranosyl)-N-octadecyl-dodecanoamide J.67 N-(2-(N-benzyloxycarbonyl-L-leucinamido)-2-deoxy-β-D-glucopyranosyl)-N-octadecyl-tetradecanoamide J.68 N-(2-(N-benzyloxycarbonyl-L-leucinamido)-2-deoxy-β-D-glucopyranosyl)-N-octadecyl-hexadecanoamide J.69 N-(2-(N-benzyloxycarbonyl-L-leucinamido)-2-deoxy-β-D-glucopyranosyl)-N-octadecyl-octadecanoamide J.70 N-(2-(N-benzyloxycarbonyl-sarcosinamido)-2-deoxy-β-D-glucopyranosyl)-N-dodecyl-dodecanoamide J.71 N-(2-(N-benzyloxycarbonyl-sarcosinamido)-2-deoxy-β-D-glucopyranosyl)-N-dodecyl-octadecanoamide J.72 N-(2-(N-benzyloxycarbonyl-sarcosinamido)-2-deoxy-β-D-glucopyranosyl)-N-tetradecyl-dodecanoamide J.73 N-(2-(N-benzyloxycarbonyl-sarcosinamido)-2-deoxy-β-D-glucopyranosyl)-N-tetradecyl-octadecanoamide J.74 N-(2-(N-benzyloxycarbonyl-sarcosinamido)-2-deoxy-β-D-glucopyranosyl)-N-octadecyl-dodecanoamide J.75 N-(2-(N-benzyloxycarbonyl-sarcosinamido)-2-deoxy-β-D-glucopyranosyl)-N-octadecyl-tetradecanoamide J.76 N-(2-(N-benzyloxycarbonyl-sarcosinamido)-2-deoxy-β-D-glucopyranosyl)-N-octadecyl-octadecanoamide J.77 N-(2-(N-benzyloxycarbonyl-O-benzyl-L-serinamido)-2-deoxy-β-D-glucopyranosyl)-N-dodecyl-dodecanoamide J.78 N-(2-(N-benzyloxycarbonyl-O-benzyl-L-serinamido)-2-deoxy-β-D-glucopyranosyl)-N-dodecyl-octadecanoamide J.79 N-(2-(N-benzyloxycarbonyl-O-benzyl-L-serinamido)-2-deoxy-β-D-glycopyranosyl)-N-tetradecyl-dodecanoamide J.80 N-(2-(N-benzyloxycarbonyl-O-benzyl-L-serinamido)-2-deoxy-β-D-glucopyranosyl)-N-tetradecyl-octadecanoamide J.81 N-(2-(N-benzyloxycarbonyl-O-benzyl-L-serinamido)-2-deoxy-β-D-glucopyranosyl)-N-octadecyl-dodecanoamide J.82 N-(2-(N-benzyloxycarbonyl-O-benzyl-L-serinamido)-2-deoxy-β-D-glucopyranosyl)-N-octadecyl-tetradecanoamide J.83 N-(2-(N-benzyloxycarbonyl-O-benzyl-L-serinamido)-2-deoxy-β-D-glucopyranosyl)-N-octadecyl-octadecanoamide J.84 N-(2-(2,5-di-N-benzyloxycarbonyl-L-lysinamido)-2-deoxy-β-d-glycopyranosyl)-N-dodecyl-dodecanoamide J.85 N-(2-(2,5-di-N-benzyloxycarbonyl-L-lysinamido)-2-deoxy-β-D-glucopyranosyl)-N-dodecyl-octadecanoamide J.86 N-(2-(2,5-di-N-benzyloxycarbonyl-L-lysinamido)-2-deoxy-β-D-glucopyranosyl)-N-tetradecyl-dodecanoamide J.87 N-(2-(2,5-di-N-benzyloxycarbonyl-L-lysinamido)-2-deoxy-β-D-glucopyranosyl)-N-tetradecyl-octadecanoamide J.88 N-(2-(2,5-di-N-benzyloxycarbonyl-L-lysinamido)-2-deoxy-β-D-glucopyranosyl)-N-octadecyl-dodecanoamide J.89 N-(2-(2,5-di-N-benzyloxycarbonyl-L-lysinamido)-2-deoxy-β-D-glucopyranosyl)-N-octadecyl-tetradecanoamide J.90 N-(2-(2,5-di-N-benzyloxycarbonyl-L-lysinamido)-2-deoxy-β-D-glycopyranosyl)-N-octadecyl-octadecanoamide J.91 N-(2-(benzyl-2-N-benzyloxycarbonyl-L-aspartoylamido-2-deoxy-β-D-glycopyranosyl)-N-dodecyl-dodecanoamide J.92 N-(2-(benzyl-2-N-benzyloxycarbonyl-L-aspartoylamido)-2-deoxy-β-D-glucopyranosyl)-N-dodecyl-octadecanoamide J.93 N-(2-(benzyl-2-N-benzyloxycarbonyl-L-aspartoylamido)-2-deoxy-β-D-glucopyranosyl)-N-tetradecyl-dodecanoamide J.94 N-(2-(benzyl-2-N-benzyloxycarbonyl-L-aspartoylamido)-2-deoxy-β-D-glucopyranosyl)-N-tetradecyl-octadecanoamide J.95 N-(2-(benzyl-2-N-benzyloxycarbonyl-L-aspartoylamido)-2-deoxy-β-D-glucopyranosyl)-N-octadecyl-dodecanoamide J.96 N-(2-(benzyl-2-N-benzyloxycarbonyl-L-aspartoylamido)-2-deoxy-β-D-glycopyranosyl)-N-octadecyl-tetradecanoamide J.97 N-(2-(benzyl-2-N-benzyloxycarbonyl-L-aspartoylamido)-2-deoxy-β-D-glucopyranosyl)-N-octadecyl-octadecanoamide J.98 N-(2-(2-N-benzyloxycarbonyl-5-O-benzyl-L-glutaminamido)-2-deoxy-β-D-glucopyranosyl)-N-dodecyl-dodecanoamide J.99 N-(2-(2-N-benzyloxycarbonyl-5-O-benzyl-L-glutaminamido)-2-deoxy-β-D-glucopyranosyl)-N-dodecyl-octadecanoamide J.100 N-(2-(2-N-benzyloxycarbonyl-5-O-benzyl-L-glutaminamido)-2-deoxy-β-D-glucopyranosyl)-N-tetradecyl-dodecanoamide J.101 N-(2-(2-N-benzyloxycarbonyl-5-O-benzyl-L-glutaminamido)-2-deoxy-β-D-glucopyranosyl)-N-tetradecyl-octadecanoamide J.102 N-(2-(2-N-benzyloxycarbonyl-5-O-benzyl-L-glutaminamido)-2-deoxy-β-D-glucopyranosyl)-N-octadecyl-dodecanoamide J.103 N-(2-(2-N-benzyloxycarbonyl-5-O-benzyl-L-glutaminamido)-2-deoxy-β-D-glucopyranosyl)-N-octadecyl-tetradecanoamide J.104 N-(2-(2-N-benzyloxycarbonyl-5-O-benzyl-L-glutaminamido)-2-deoxy-β-D-glucopyranosyl)-N-octadecyl-octadecanoamide J.105 N-(2-(N-benzyloxycarbonyl-glycinamido)-2-deoxy-β-D-galactopyranosyl)-N-dodecyl-dodecanoamide J.106 N-(2-(N-benzyloxycarbonyl-glycinamido)-2-deoxy-β-D-galactopyranosyl)-N-dodecyl-octadecanoamide J.107 N-(2-(N-benzyloxycarbonyl-glycinamido)-2-deoxy-β-D-galactopyranosyl)-N-tetradecyl-dodecanoamide J.108 N-(2-(N-benzyloxycarbonyl-glycinamido)-2-deoxy-β-D-galactopyranosyl)-N-tetradecyl-octadecanoamide J.109 N-(2-(N-benzyloxycarbonyl-glycinamido)-2-deoxy-β-D-galactopyranosyl)-N-octadecyl-dodecanoamide J.110 N-(2-(N-benzyloxycarbonyl-glycinamido)-2-deoxy-β-D-galactopyranosyl)-N-octadecyl-tetradecanoamide J.111 N-(2-(N-benzyloxycarbonyl-glycinamido)-2-deoxy-β-D-galactopyranosyl)-N-octadecyl-octadecanoamide J.112 N-(2-(N-benzyloxycarbonyl-L-alaninamido)-2-deoxy-β-D-galactopyranosyl)-N-dodecyl-dodecanoamide J.113 N-(2-(N-benzyloxycarbonyl-L-alaninamido)-2-deoxy-β-D-galactopyranosyl)-N-dodecyl-octadecanoamide J.114 N-(2-(N-benzyloxycarbonyl-L-alaninamido)-2-deoxy-β-D-galactopyranosyl)-N-tetradecyl-dodecanoamide J.115 N-(2-(N-benzyloxycarbonyl-L-alaninamido)-2-deoxy-β-D-galactopyranosyl)-N-tetradecyl-octadecanoamide J.116 N-(2-(N-benzyloxycarbonyl-L-alaninamido)-2-deoxy-β-D-galactopyranosyl)-N-octadecyl-dodecanoamide J.117 N-(2-(N-benzyloxycarbonyl-L-alaninamido)-2-deoxy-β-D-galactopyranosyl)-N-octadecyl-tetradecanoamide J.118 N-(2-(N-benzyloxycarbonyl-L-alaninamido)-2-deoxy-β-D-galactopyranosyl)-N-octadecyl-octadecanoamide J.119 N-(2-(N-benzyloxycarbonyl-L-leucinamido)-2-deoxy-β-D-galactopyranosyl)-N-dodecyl-dodecanoamide J.120 N-(2-(N-benzyloxycarbonyl-L-leucinamido)-2-deoxy-β-D-galactopyranosyl)-N-dodecyl-octadecanoamide J.121 N-(2-(N-benzyloxycarbonyl-L-leucinamido)-2-deoxy-β-D-galactopyranosyl)-N-tetradecyl-dodecanoamide J.122 N-(2-(N-benzyloxycarbonyl-L-leucinamido)-2-deoxy-β-D-galactopyranosyl)-N-tetradecyl-octadecanoamide J.123 N-(2-(N-benzyloxycarbonyl-L-leucinamido)-2-deoxy-β-D-galactopyranosyl)-N-octadecyl-dodecanoamide J.124 N-(2-(N-benzyloxycarbonyl-L-leucinamido)-2-deoxy-β-D-galactopyranosyl)-N-octadecyl-tetradecanoamide J.125 N-(2-(N-benzyloxycarbonyl-L-leucinamido)-2-deoxy-β-D-galactopyranosyl)-N-octadecyl-octadecanoamide The following compounds of the general structure XII (X=—O—) can be obtained by the method detailed under J.

J.126 O-dodecyl N-(2-(N-benzyloxycarbonyl-glycinamido)-2-deoxy-β-D-glucopyranosyl)-N-dodecyl-carbamate J.127 O-tetradecyl N-(2-(N-benzyloxycarbonyl-glycinamido)-2-deoxy-β-D-glucopyranosyl)-N-dodecyl-carbamate J.128 O-octadecyl N-(2-(N-benzyloxycarbonyl-glycinamido)-2-deoxy-β-D-glucopyranosyl)-N-dodecyl-carbamate J.129 O-dodecyl N-(2-(N-benzyloxycarbonyl-glycinamido)-2-deoxy-β-D-glucopyranosyl)-N-tetradecyl-carbamate J.130 O-octadecyl N-(2-(N-benzyloxycarbonyl-glycinamido)-2-deoxy-β-D-glucopyranosyl)-N-tetradecyl-carbamate J.131 O-dodecyl N-(2-(N-benzyloxycarbonyl-glycinamido)-2-deoxy-β-D-glucopyranosyl)-N-octadecyl-carbamate J.132 O-tetradecyl N-(2-(N-benzyloxycarbonyl-glycinamido)-2-deoxy-β-D-glucopyranosyl)-N-octadecyl-carbamate J.133 O-octadecyl N-(2-(N-benzyloxycarbonyl-glycinamido)-2-deoxy-β-D-glucopyranosyl)-N-octadecyl-carbamate J.134 O-dodecyl N-(2-(N-benzyloxycarbonyl-L-alaninamido)-2-deoxy-β-D-glucopyranosyl)-N-dodecyl-carbamate J.135 O-tetradecyl N-(2-(N-benzyloxycarbonyl-L-alaninamido)-2-deoxy-β-D-glycopyranosyl)-N-dodecyl-carbamate J.136 O-octadecyl N-(2-(N-benzyloxycarbonyl-L-alaninamido)-2-deoxy-β-D-glucopyranosyl)-N-dodecyl-carbamate J.137 O-dodecyl N-(2-(N-benzyloxycarbonyl-L-alaninamido)-2-deoxy-β-D-glucopyranosyl)-N-tetradecyl-carbamate J.138 O-octadecyl N-(2-(N-benzyloxycarbonyl-L-alaninamido)-2-deoxy-β-D-glucopyranosyl)-N-tetradecyl-carbamate J.139 O-dodecyl N-(2-(N-benzyloxycarbonyl-L-alaninamido)-2-deoxy-β-D-glucopyranosyl)-N-octadecyl-carbamate J.140 O-tetradecyl N-(2-(N-benzyloxycarbonyl-L-alaninamido)-2-deoxy-β-D-glucopyranosyl)-N-octadecyl-carbamate J.141 O-octadecyl N-(2-(N-benzyloxycarbonyl-L-alaninamido)-2-deoxy-β-D-glucopyranosyl)-N-octadecyl-carbamate J.142 O-dodecyl N-(2-(N-benzyloxycarbonyl-L-leucinamido)-2-deoxy-β-D-glucopyranosyl)-N-dodecyl-carbamate J.143 O-tetradecyl N-(2-(N-benzyloxycarbonyl-L-leucinamido)-2-deoxy-β-D-glucopyranosyl)-N-dodecyl-carbamate J.144 O-octadecyl N-(2-(N-benzyloxycarbonyl-L-leucinamido)-2-deoxy-β-D-glucopyranosyl)-N-dodecyl-carbamate J.145 O-dodecyl N-(2-(N-benzyloxycarbonyl-L-leucinamido)-2-deoxy-β-D-glucopyranosyl)-N-tetradecyl-carbamate J.146 O-octadecyl N-(2-(N-benzyloxycarbonyl-L-leucinamido)-2-deoxy-β-D-glucopyranosyl)-N-tetradecyl-carbamate J.147 O-dodecyl N-(2-(N-benzyloxycarbonyl-L-leucinamido)-2-deoxy-β-D-glucopyranosyl)-N-octadecyl-carbamate J.148 O-tetradecyl N-(2-(N-benzyloxycarbonyl-L-leucinamido)-2-deoxy-β-D-glucopyranosyl)-N-octadecyl-carbamate J.149 O-octadecyl N-(2-(N-benzyloxycarbonyl-L-leucinamido)-2-deoxy-β-D-glucopyranosyl)-N-octadecyl-carbamate J.150 O-dodecyl N-(2-(N-benzyloxycarbonyl-glycinamido)-2-deoxy-β-D-galactopyranosyl)-N-dodecyl-carbamate J.151 O-tetradecyl N-(2-(N-benzyloxycarbonyl-glycinamido)-2-deoxy-β-D-galactopyranosyl)-N-dodecyl-carbamate J.152 O-octadecyl N-(2-(N-benzyloxycarbonyl-glycinamido)-2-deoxy-β-D-galactopyranosyl)-N-dodecyl-carbamate J.153 O-dodecyl N-(2-(N-benzyloxycarbonyl-glycinamido)-2-deoxy-β-D-galactopyranosyl)-N-tetradecyl-carbamate J.154 O-octadecyl N-(2-(N-benzyloxycarbonyl-glycinamido)-2-deoxy-β-D-galactopyranosyl)-N-tetradecyl-carbamate J.155 O-dodecyl N-(2-(N-benzyloxycarbonyl-glycinamido)-2-deoxy-β-D-galactopyranosyl)-N-octadecyl-carbamate J.156 O-tetradecyl N-(2-(N-benzyloxycarbonyl-glycinamido)-2-deoxy-β-D-galactopyranosyl)-N-octadecyl-carbamate J.157 O-octadecyl N-(2-(N-benzyloxycarbonyl-glycinamido)-2-deoxy-β-D-galactopyranosyl)-N-octadecyl-carbamate The following compounds of the general structure XII (X=—NH—) can be obtained by the methods detailed under J.

J.158 N-(2-(N-benzyloxycarbonyl-glycinamido)-2-deoxy-β-D-glucopyranosyl)-N-dodecyl-N'-dodecyl-urea J.159 N-(2-(N-benzyloxycarbonyl-glycinamido)-2-deoxy-β-D-glucopyranosyl)-N-dodecyl-N'-tetradecyl-urea J.160 N-(2-(N-benzyloxycarbonyl-glycinamido)-2-deoxy-β-D-glucopyranosyl)-N-dodecyl-N'-octadecyl-urea J.161 N-(2-(N-benzyloxycarbonyl-glycinamido)-2-deoxy-β-D-glucopyranosyl)-N-tetradecyl-N'-dodecyl-urea J.162 N-(2-(N-benzyloxycarbonyl-glycinamido)-2-deoxy-β-D-glucopyranosyl)-N-tetradecyl-N'-octadecyl-urea J.163 N-(2-(N-benzyloxycarbonyl-glycinamido)-2-deoxy-β-D-glucopyranosyl)-N-octadecyl-N'-dodecyl-urea J.164 N-(2-(N-benzyloxycarbonyl-glycinamido)-2-deoxy-β-D-glucopyranosyl)-N-octadecyl-N'-tetradecyl-urea J.165 N-(2-(N-benzyloxycarbonyl-glycinamido)-2-deoxy-β-D-glucopyranosyl)-N-octadecyl-N'-octadecyl-urea J.166 N-(2-(N-benzyloxycarbonyl-L-alaninamido)-2-deoxy-β-D-glucopyranosyl)-N-dodecyl-N'-dodecyl-urea J.167 N-(2-(N-benzyloxycarbonyl-L-alaniamido)-2-deoxy-β-D-glucopyranosyl)-N-dodecyl-N'-tetradecyl-urea J.168 N-(2-(N-benzyloxycarbonyl-L-alaninamido)-2-deoxy-β-D-glucopyranosyl)-N-dodecyl-N'-octadecyl-urea J.169 N-(2-(N-benzyloxycarbonyl-L-alaninamido)-2-deoxy-β-D-glucopyranosyl)-N-tetradecyl-N'-dodecyl-urea J.170 N-(2-(N-benzyloxycarbonyl-L-alaninamido)-2-deoxy-β-D-glucopyranosyl)-N-tetradecyl-N'-octadecyl-urea J.171 N-(2-(N-benzyloxycarbonyl-L-alaninamido)-2-deoxy-β-D-glucopyranosyl)-N-octadecyl-N'-dodecyl-urea J.172 N-(2-(N-benzyloxycarbonyl-L-alaninamido)-2-deoxy-β-D-glucopyranosyl)-N-octadecyl-N'-tetradecyl-urea J.173 N-(2-(N-benzyloxycarbonyl-L-alaninamido)-2-deoxy-β-D-glucopyranosyl)-N-octadecyl-N'-octadecyl-urea J.174 N-(2-(N-benzyloxycarbonyl-L-leucinamido)-2-deoxy-β-D-glucopyranosyl)-N-dodecyl-N'-dodecyl-urea J.175 N-(2-(N-benzyloxycarbonyl-L-leucinamido)-2-deoxy-β-D-glucopyranosyl)-N-dodecyl-N'-tetradecyl-urea J.176 N-(2-(N-benzyloxycarbonyl-L-leucinamido)-2-deoxy-β-D-glucopyranosyl)-N-dodecyl-N'-octadecyl-urea J.177 N-(2-(N-benzyloxycarbonyl-L-leucinamido)-2-deoxy-β-D-glucopyranosyl)-N-tetradecyl-N'-dodecyl-urea J.178 N-(2-(N-benzyloxycarbonyl-L-leucinamido)-2-deoxy-β-D-glucopyranosyl)-N-tetradecyl-N'-octadecyl-urea J.179  N-(2-(N-benzyloxycarbonyl-L-leucinamido)-2-deoxy-β-D-glucopyranosyl)-N-octadecyl-N'-dodecyl-urea J.180  N-(2-(N-benzyloxycarbonyl-L-leucinamido)-2-deoxy-β-D-glucopyranosyl)-N-octadecyl-N'-tetradecyl-urea J.181  N-(2-(N-benzyloxycarbonyl-L-leucinamido)-2-deoxy-β-D-glucopyranosyl)-N-octadecyl-N'-octadecyl-urea J.182  N-(2-(N-benzyloxycarbonyl-glycinamido)-2-deoxy-β-D-galactopyranosyl)-N-dodecyl-N'-dodecyl-urea J.183  N-(2-(N-benzyloxycarbonyl-glycinamido)-2-deoxy-β-D-galactopyranosyl)-N-dodecyl-N'-tetradecyl-urea J.184  N-(2-(N-benzyloxycarbonyl-glycinamido)-2-deoxy-β-D-galactopyranosyl)-N-dodecyl-N'-octadecyl-urea J.185  N-(2-(N-benzyloxycarbonyl-glycinamido)-2-deoxy-β-D-galactopyranosyl)-N-tetradecyl-N'-dodecyl-urea J.186  N-(2-(N-benzyloxycarbonyl-glycinamido)-2-deoxy-β-D-galactopyranosyl)-N-tetradecyl-N'-octadecyl-urea J.187  N-(2-(N-benzyloxycarbonyl-glycinamido)-2-deoxy-β-D-galactopyranosyl)-N-octadecyl-N'-dodecyl-urea J.188  N-(2-(N-benzyloxycarbonyl-glycinamido)-2-deoxy-β-D-galactopyranosyl)-N-octadecyl-N'-tetradecyl-urea J.189  N-(2-(N-benzyloxycarbonyl-glycinamido)-2-deoxyβ-D-galactopyranosyl)-N-octadecyl-N'-octadecyl-urea The following compounds of the general structure I (X=—CH$_2$—) can be obtained in the form of their acetic acid salts by the method detailed under M.

M.1  N-(2-glycinamido-2-deoxy-β-D-glucopyranosyl)-N-dodecyl-dodecanoamide

M.2  N-(2-glycinamido-2-deoxy-β-D-glucopyranosyl)-N-dodecyl-tetradecanoamide

M.3  N-(2-glycinamido-2-deoxy-β-D-glucopyranosyl)-N-dodecyl-hexadecanoamide

M.4  N-(2-glycinamido-2-deoxy-β-D-glucopyranosyl)-N-dodecyl-octadecanoamide

M.5  N-(2-glycinamido-2-deoxy-β-D-glucopyranosyl)-N-tetradecyl-dodecanoamide

M.6  N-(2-glycinamido-2-deoxy-β-D-glucopyranosyl)-N-tetradecyl-tetradecanoamide

M.7  N-(2-glycinamido-2-deoxy-β-D-glucopyranosyl)-N-tetradecyl-hexadecanoamide

M.8  N-(2-glycinamido-2-deoxy-β-D-glucopyranosyl)-N-tetradecyl-octadecanoamide

M.9  N-(2-glycinamido-2-deoxy-β-D-glucopyranosyl)-N-hexadecyl-dodecanoamide

M.10  N-(2-glycinamido-2-deoxy-β-D-glucopyranosyl)-N-hexadecyl-tetradecanoamide

M.11  N-(2-glycinamido-2-deoxy-β-D-glucopyranosyl)-N-hexadecyl-hexadecanoamide

M.12  N-(2-glycinamido-2-deoxy-β-D-glucopyranosyl)-N-hexadecyl-octadecanoamide

M.13  N-(2-glycinamido-2-deoxy-β-D-glucopyranosyl)-N-octadecyl-dodecanoamide

M.14  N-(2-glycinamido-2-deoxy-β-D-glucopyranosyl)-N-octadecyl-tetradecanoamide

M.15  N-(2-glycinamido-2-deoxy-β-D-glucopyranosyl)-N-octadecyl-hexadecanoamide

M.16  N-(2-glycinamido-2-deoxy-β-D-glucopyranosyl)-N-octadecyl-octadecanoamide

M.17  N-(2-L-alaninamido-2-deoxy-β-D-glucopyranosyl)-N-dodecyl-dodecanoamide

M.18  N-(2-L-alaninamido-2-deoxy-β-D-glucopyranosyl)-N-dodecyl-tetradecanoamide

M.19  N-(2-L-alaninamido-2-deoxy-β-D-glucopyranosyl)-N-dodecyl-hexadecanoamide

M.20  N-(2-L-alaninamido-2-deoxy-β-D-glucopyranosyl)-N-dodecyl-octadecanoamide

M.21  N-(2-L-alaninamido-2-deoxy-β-D-glucopyranosyl)-N-tetradecyl-dodecanoamide

M.22  N-(2-L-alaninamido-2-deoxy-β-D-glucopyranosyl)-N-tetradecyl-tetradecanoamide M.23  N-(2-L-alaninamido-2-deoxy-β-D-glucopyranosyl)-N-tetradecyl-hexadecanoamide M.24  N-(2-L-alaninamido-2-deoxy-β-D-glucopyranosyl)-N-tetradecyl-octadecanoamide M.25  N-(2-L-alaninamido-2-deoxy-β-D-glucopyranosyl)-N-hexadecyl-dodecanoamide M.26  N-(2-L-alaninamido-2-deoxy-β-D-glucopyranosyl)-N-hexadecyl-tetradecanoamide M.27  N-(2-L-alaninamido-2-deoxy-β-D-glucopyranosyl)-N-hexadecyl-hexadecanoamide M.28  N-(2-L-alaninamido-2-deoxy-β-D-glucopyranosyl)-N-hexadecyl-octadecanoamide M.29  N-(2-L-alaninamido-2-deoxy-β-D-glucopyranosyl)-N-octadecyl-dodecanoamide M.30  N-(2-L-alaninamido-2-deoxy-β-D-glucopyranosyl)-N-octadecyl-tetradecanoamide M.31  N-(2-L-alaninamido-2-deoxy-β-D-glucopyranosyl)-N-octadecyl-hexadecanoamide M.32  N-(2-L-alaninamido-2-deoxy-β-D-glucopyranosyl)-N-octadecyl-octadecanoamide M.33  N-(2-D-alaninamido-2-deoxy-β-D-glucopyranosyl)-N-dodecyl-dodecanoamide M.34  N-(2-D-alaninamido-2-deoxy-β-D-glucopyranosyl)-N-dodecyl-octadecanoamide M.35  N-(2-D-alaninamido-2-deoxy-β-D-glucopyranosyl)-N-tetradecyl-dodecanoamide M.36  N-(2-D-alaninamido-2-deoxy-β-D-glucopyranosyl)-N-tetradecyl-octadecanoamide M.37  N-(2-D-alaninamido-2-deoxy-β-D-glucopyranosyl)-N-octadecyl-dodecanoamide M.38  N-(2-D-alaninamido-2-deoxy-β-D-glucopyranosyl)-N-octadecyl-tetradecanoamide M.39  N-(2-D-alaninamido-2-deoxy-β-D-glucopyranosyl)-N-octadecyl-octadecanoamide M.40  N-(2-L-phenylalaninamido-2-deoxy-β-D-glucopyranosyl)-N-dodecyl-dodecanoamide M.41  N-(2L-phenylalaninamido-2-deoxy-β-D-glucopyranosyl)-N-dodecyl-octadecanoamide M.42  N-(2-L-phenylalaninamido-2-deoxy-β-D-glucopyranosyl)-N-tetradecyl-dodecanoamide M.43  N-(2-L-phenylalaninamido-2-deoxy-β-D-glucopyranosyl)-N-tetradecyl-octadecanoamide M.44  N-(2-L-phenylalaninamido-2-deoxy-β-D-glucopyranosyl)-N-octadecyl-dodecanoamide M.45  N-(2-L-phenylalaninamido-2-deoxy-β-D-glucopyranosyl)-N-octadecyl-tetradecanoamide M.46  N-(2-L-phenylalaninamido-2-deoxy-β-D-glucopyranosyl)-N-octadecyl-octadecanoamide M.47  N-(2-L-valinamido-2-deoxy-β-D-glucopyranosyl)-N-dodecyl-dodecanoamide M.48  N-(2-L-valinamido-2-deoxy-β-D-glucopyranosyl)-N-dodecyl-octadecanoamide M.49  N-(2-L-valinamido-2-deoxy-β-D-glucopyranosyl)-N-tetradecyl-dodecanoamide M.50  N-(2-L-valinamido-2-deoxy-β-D-glucopyranosyl)-N-tetradecyl-octadecanoamide M.51 N-(2-L-valinamido-2-deoxy-β-D-glucopyranosyl)-N-octadecyl-dodecanoamide
M.52 N-(2-L-valinamido-2-deoxy-β-D-glucopyranosyl)-N-octadecyl-tetradecanoamide
M.53 N-(2-L-valinamido-2-deoxy-β-D-glucopyranosyl)-N-octadecyl-octadecanoamide
M.54 N-(2-L-leucinamido-2-deoxy-β-D-glucopyranosyl)-N-dodecyl-dodecanoamide
M.55 N-(2-L-leucinamido-2-deoxy-β-D-glucopyranosyl)-N-dodecyl-tetradecanoamide
M.56 N-(2-L-leucinamido-2-deoxy-β-D-glucopyranosyl)-N-dodecyl-hexadecanoamide
M.57 N-(2-L-leucinamido-2-deoxy-β-D-glucopyranosyl)-N-dodecyl-octadecanoamide
M.58 N-(2-L-leucinamido-2-deoxy-β-D-glucopyranosyl)-N-tetradecyl-dodecanoamide
M.59 N-(2-L-leucinamido-2-deoxy-β-D-glucopranosyl)-N-tetradecyl-tetradecanoamide
M.60 N-(2-L-leucinamido-2-deoxy-β-D-glucopyranosyl)-N-tetradecyl-hexadecanoamide
M.61 N-(2-L-leucinamido-2-deoxy-β-D-glucopyranosyl)-N-tetradecyl-octadecanoamide
M.62 N-(2-L-leucinamido-2-deoxy-β-D-glucopyranosyl)-N-hexadecyl-dodecanoamide
M.63 N-(2-leucinamido-2-deoxy-β-D-glucopyranosyl)-N-hexadecyl-tetradecanoamide
M.64 N-(2-L-leucinamido-2-deoxy-β-D-glucopyranosyl)-N-hexadecyl-hexadecanoamide
M.65 N-(2-L-leucinamido-2-deoxy-β-D-glucopyranosyl)-N-hexadecyl-octadecanoamide
M.66 N-(2-L-leucinamido-2-deoxy-β-D-glucopyranosyl)-N-octadecyl-dodecanoamide
M.67 N-(2-L-leucinamido-2-deoxy-β-D-glucopyranosyl)-N-octadecyl-tetradecanoamide
M.68 N-(2L-leucinamido-2-deoxy-β-D-glucopyranosyl)-N-octadecyl-hexadecanoamide
M.69 N-(2-L-leucinamido-2-deoxy-β-D-glucopyranosyl)-N-octadecyl-octadecanoamide
M.70 N-(2-sarcosinamido-2-deoxy-β-D-glucopyranosyl)-N-dodecyl-dodecanoamide
M.71 N-(2-sarcosinamido-2-deoxy-β-D-glucopyranosyl)-N-dodecyl-octadecanoamide
M.72 N-(2-sarcosinamido-2-deoxy-β-D-glucopyranosyl)-N-tetradecyl-dodecanoamide
M.73 N-(2-sarcosinamido-2-deoxy-β-D-glucopyranosyl)-N-tetradecyl-octadecanoamide
M.74 N-(2-sarcosinamido-2-deoxy-β-D-glucopyranosyl)-N-octadecyl-dodecanoamide
M.75 N-(2-sarcosinamido-2-deoxy-β-D-glucopyranosyl)-N-octadecyl-tetradecanoamide
M.76 N-(2-sarcosinamido-2-deoxy-β-D-glucopyranosyl)-N-octadecyl-octadecanoamide
M.77 N-(2-L-serinamido-2-deoxy-β-D-glucopyranosyl)-N-dodecyl-dodecanoamide
M.78 N-(2-L-serinamido-2-deoxy-β-D-glucopyranosyl)-N-dodecyl-octadecanoamide
M.79 N-(2-L-serinamido-2-deoxy-β-D-glucopyranosyl)-N-tetradecyl-dodecanoamide
M.80 N-(2-L-serinamido-2-deoxy-β-D-glucopyranosyl)-N-tetradecyl-octadecanoamide
M.81 N-(2-L-serinamido-2-deoxy-β-D-glucopyranosyl)-N-octadecyl-dodecanoamide
M.82 N-(2-L-serinamido-2-deoxy-β-D-glucopyranosyl)-N-octadecyl-tetradecanoamide
M.83 N-(2-L-serinamido-2-deoxy-β-D-glucopyranosyl)-N-octadecyl-octadecanoamide
M.84 N-(2-L-lysinamido-2-deoxy-β-D-glucopyranosyl)-N-dodecyl-dodecanoamide
M.85 N-(2-L-lysinamido-2-deoxy-β-D-glucopyranosyl)-N-dodecyl-octadecanoamide
M.86 N-(2-L-lysinamido-2-deoxy-β-D-glucopyranosyl)-N-tetradecyl-dodecanoamide
M.87 N-(2-L-lysinamido-2-deoxy-β-D-glucopyranosyl)-N-tetradecyl-octadecanoamide
M.88 N-(2-L-lysinamido-2-deoxy-β-D-glucopyranosyl)-N-octadecyl-dodecanoamide
M.89 N-(2-L-lysinamido-2-deoxy-β-D-glucopyranosyl)-N-octadecyl-tetradecanoamide
M.90 N-(-2-L-lysinamido-2-deoxy-β-D-glucopyranosyl)-N-octadecyl-octadecanoamide
M.91 N-(2-L-asparaginamido-2-deoxy-β-D-glucopyranosyl)-N-dodecyl-dodecanoamide
M.92 N-(2-L-asparaginamido-2-deoxy-β-D-glucopyranosyl)-N-dodecyl-octadecanoamide
M.93 N-(2-L-asparaginamido-2-deoxy-β-D-glucopyranosyl)-N-tetradecyl-dodecanoamide
M.94 N-(2-L-asparaginamido-2-deoxy-β-D-glucopyranosyl)-N-tetradecyl-octadecanoamide
M.95 N-(2-L-asparaginamido-2-deoxy-β-D-glucopyranosyl)-N-octadecyl-dodecanoamide
M.96 N-(2-L-asparaginamido-2-deoxy-β-D-glucopyranosyl)-N-octadecyl-tetradecanoamide
M.97 N-(2-L-asparaginamido-2-deoxy-β-D-glucopyranosyl)-N-octadecyl-octadecanoamide
M.98 N(-2-L-glutaminamido-2-deoxy-β-D-glucopyranosyl)-N-dodecyl-dodecanoamide
M.99 N(-2-L-glutaminamido-2-deoxy-β-D-glucopyranosyl)-N-dodecyl-octadecanoamide
M.100 N(-2-L-glutaminamido-2-deoxy-β-D-glucopyranosyl)-N-tetradecyl-dodecanoamide
M.101 N(-2-L-glutaminamido-2-deoxy-β-D-glucopyranosyl)-N-tetradecyl-octadecanoamide
M.102 N(-2-L-glutaminamido-2-deoxy-β-D-glucopyranosyl)-N-octadecyl-dodecanoamide
M.103 N(-2-L-glutaminamido-2-deoxy-β-D-glucopyranosyl)-N-octadecyl-tetradecanoamide
M.104 N(-2-L-glutaminamido-2-deoxy-β-D-glucopyranosyl)-N-octadecyl-octadecanoamide
M.105 N-(2-glycinamido-2-deoxy-β-D-galactopyranosyl)-N-dodecyl-dodecanoamide
M.106 N-(2-glycinamido-2-deoxy-β-D-galactopyranosyl)-N-dodecyl-octadecanoamide
M.107 N-(2-glycinamido-2-deoxy-β-D-galactopyranosyl)-N-tetradecyl-dodecanoamide
M.108 N-(2-glycinamido-2-deoxy-β-D-galactopyranosyl)-N-tetradecyl-octadecanoamide
M.109 N-(2-glycinamido-2-deoxy-β-D-galactopyranosyl)-N-octadecyl-dodecanoamide
M.110 N-(2-glycinamido-2-deoxy-β-D-galactopyranosyl)-N-N-octadecyl-tetradecanoamide
M.111 N-(2-glycinamido-2-deoxy-β-D-galactopyranosyl)-N-octadecyl-octadecanoamide
M.112 N-(2-L-alaninamido-2-deoxy-β-D-galactopyranosyl)-N-dodecyl-dodecanoamide
M.113 N-(2-L-alaninamido-2-deoxy-β-D-galactopyranosyl)-N-dodecyl-octadecanoamide
M.114 N-(2-L-alaninamido-2-deoxy-β-D-galactopyranosyl)-N-tetradecyl-dodecanoamide
M.115 N-(2-L-alaninamido-2-deoxy-β-D-galactopyranosyl)-N-tetradecyl-octadecanoamide
M.116 N-(2-L-alaninamido-2-deoxy-β-D-galactopyranosyl)-N-octadecyl-dodecanoamide
M.117 N-(2-L-alaninamido-2-deoxy-β-D-galactopyranosyl)-N-octadecyl-tetradecanoamide
M.118 N-(2-L-alaninamido-2-deoxy-β-D-galactopyranosyl)-N-octadecyl-octadecanoamide M.119 N-(2-L-leucinamido-2-deoxy-β-D-galactopyranosyl)-N-dodecyl-dodecanoamide
M.120 N-(2-L-leucinamido-2-deoxy-β-D-galactopyranosyl)-N-dodecyl-octadecanoamide
M.121 N-(2-L-leucinamido-2-deoxy-β-D-galactopyranosyl)-N-tetradecyl-dodecanoamide
M.122 N-(2-L-leucinamido-2-deoxy-β-D-galactopyranosyl)-N-tetradecyl-octadecanoamide
M.123 N-(2-L-leucinamido-2-deoxy-β-D-galactopyranosyl)-N-octadecyl-dodecanoamide
M.124 N-(2-L-leucinamido-2-deoxy-β-D-galactopyranosyl)-N-octadecyl-tetradecanoamide
M.125 N-(2-L-leucinamido-2-deoxy-β-D-galactopyranosyl)-N-octadecyl-octadecanoamide The following compounds of the general structure I (X=—O—) can be obtained by the method detailed under M.

M.126 O-dodecyl N-(2-glycinamido-2-deoxy-β-D-glucopyranosyl)-N-dodecyl-carbamate
M.127 O-tetradecyl N-(2-glycinamido-2-deoxy-β-D-glucopyranosyl)-N-dodecyl-carbamate
M.128 O-octadecyl N-(2-glycinamido-2-deoxy-β-D-glucopyranosyl)-N-dodecyl-carbamate
M.129 O-dodecyl N-(2-glycinamido-2-deoxy-β-D-glucopyranosyl)-N-tetradecyl-carbamate
M.130 O-octadecyl N-(2-glycinamido-2-deoxy-β-D-glucopyranosyl)-N-tetradecyl-carbamate
M.131 O-dodecyl N-(2-glycinamido-2-deoxy-β-D-glucopyranosyl)-N-octadecyl-carbamate
M.132 O-tetradecyl N-(2-glycinamido-2-deoxy-β-D-glucopyranosyl)-N-octadecyl-carbamate
M.133 O-octadecyl N-(2-glycinamido-2-deoxy-β-D-glucopyranosyl)-N-octadecyl-carbamate
M.134 O-dodecyl N-(2L-alaninamido-2-deoxy-β-D-glucopyranosyl)-N-dodecyl-carbamate
M.135 O-tetradecyl N-(2-L-alaninamido-2-deoxy-β-D-glucopyranosyl)-N-dodecyl-carbamate
M.136 O-octadecyl N-(2-L-alaninamido-2-deoxy-β-D-glucopyranosyl)-N-dodecyl-carbamate
M.137 O-dodecyl N-(2-L-alaninamido-2-deoxy-β-D-glucopyranosyl)-N-tetradecyl-carbamate
M.138 O-octadecyl N-(2-L-alaninamido-2-deoxy-β-D-glucopyranosyl)-N-tetradecyl-carbamate
M.139 O-dodecyl N-(2-L-alaninamido-2-deoxy-β-D-glucopyranosyl)-N-octadecyl-carbamate
M.140 O-tetradecyl N-(2-L-alaninamido-2-deoxy-β-D-glucopyranosyl)-N-octadecyl-carbamate
M.141 O-octadecyl N-(2-L-alaninamido-2-deoxy-β-D-glucopyranosyl)-N-octadecyl-carbamate
M.142 O-dodecyl N-(2-L-leucinamido-2-deoxy-β-D-glucopyranosyl)-N-dodecyl-carbamate
M.143 O-tetradecyl N-(2-L-leucinamido-2-deoxy-β-D-glucopyranosyl)-N-dodecyl-carbamate
M.144 O-octadecyl N-(2-L-leucinamido-2-deoxy-β-D-glucopyranosyl)-N-dodecyl-carbamate
M.145 O-dodecyl N-(2-L-leucinamido-2-deoxy-β-D-glucopyranosyl)-N-tetradecyl-carbamate
M.146 O-octadecyl N-(2-L-leucinamido-2-deoxy-β-D-glucopyranosyl)-N-tetradecyl-carbamate
M.147 O-dodecyl N-(2-L-leucinamido-2-deoxy-β-D-glucopyranosyl)-N-octadecyl-carbamate
M.148 O-tetradecyl N-(2-L-leucinamido-2-deoxy-β-D-glucopyranosyl)-N-octadecyl-carbamate
M.149 O-octadecyl N-(2-L-leucinamido-2-deoxy-β-D-glucopyranosyl)-N-octadecyl-carbamate
M.150 O-dodecyl N-(2-glycinamido-2-deoxy-β-D-galactopyranosyl)-N-dodecyl-carbamate
M.151 O-tetradecyl N-(2-glycinamido-2-deoxy-β-D-galactopyranosyl)-N-dodecyl-carbamate
M.152 O-octadecyl N-(2-glycinamido-2-deoxy--D-galactopyranosyl)-N-dodecyl-carbamate
M.153 O-dodecyl N-(2-glycinamido-2-deoxy-β-D-galactopyranosyl)-N-tetradecyl-carbamate
M.154 O-octadecyl N-(2-glycinamido-2-deoxy-β-D-galactopyranosyl)-N-tetradecyl-carbamate
M.155 O-dodecyl N-(2-glycinamido-2-deoxy-β-D-galactopyranosyl)-N-octadecyl-carbamate
M.156 O-tetradecyl N-(2-glycinamido-2-deoxy-β-D-galactopyranosyl)-N-octadecyl-carbamate
M.157 O-octadecyl N-(2-glycinamido-2-deoxy-β-D-galactopyranosyl)-N-octadecyl-carbamate The following compounds of the general structure I (X=—NH—) can be obtained by the method detailed under M.

M.158 N-(2-glycinamido-2-deoxy-β-D-glucopyranosyl)-N-dodecyl-N'-dodecyl-urea
M.159 N-(2-glycinamido-2-deoxy-β-D-glucopyranosyl)-N-dodecyl-N'-tetradecyl-urea
M.160 N-(2-glycinamido-2-deoxy-β-D-glucopyranosyl)-N-dodecyl-N'-octadecyl-urea
M.161 N-(2-glycinamido-2-deoxy-β-D-glucopyranosyl)-N-tetradecyl-N'-dodecyl-urea
M.162 N-(2-glycinamido-2-deoxy-β-D-glucopyranosyl)-N-tetradecyl-N'-octadecyl-urea
M.163 N-(2-glycinamido-2-deoxy-β-D-glucopyranosyl)-N-octadecyl-N'-dodecyl-urea
M.164 N-(2-glycinamido-2-deoxy-β-D-glucopyranosyl)-N-octadecyl-N'-tetradecyl-urea
M.165 N-(2-glycinamido-2-deoxy-β-D-glucopyranosyl)-N-octadecyl-N'-octadecyl-urea
M.166 N-(2-L-alaninamido-2-deoxy-β-D-glucopyranosyl)-N-dodecyl-N'-dodecyl-urea
M.167 N-(2-L-alaninamido-2-deoxy-β-D-glucopyranosyl)-N-dodecyl-N'-tetradecyl-urea
M.168 N-(2-L-alaninamido-2-deoxy-β-D-glucopyranosyl)-N-tetradecyl-N'-octadecyl-urea
M.169 N-(2-L-alaninamido-2-deoxy-β-D-glucopyranosyl)-N-tetradecyl-N'-dodecyl-urea
M.170 N-(2-L-alaninamido-2-deoxy-β-D-glucopyranosyl)-N-tetradecyl-N'-octadecyl-urea
M.171 N-(2-L-alaninamido-2-deoxy-β-D-glucopyranosyl)-N-octadecyl-N'-dodecyl-urea
M.172 N-(2-L-alaninamido-2-deoxy-β-D-glucopyranosyl)-N-octadecyl-N'-tetradecyl-urea
M.173 N-(2-L-alaninamido-2-deoxy-β-D-glucopyranosyl)-N-octadecyl-N'-octadecyl-urea
M.174 N-(2-L-leucinamido-2-deoxy-β-D-glucopyranosyl)-N-dodecyl-N'-dodecyl-urea
M.175 N-(2-L-leucinamido-2-deoxy-β-D-glucopyranosyl)-N-dodecyl-N'-tetradecyl-urea
M.176 N-(2-L-leucinamido-2-deoxy-β-D-glucopyranosyl)-N-dodecyl-N'-octadecyl-urea
M.177 N-(2-L-leucinamido-2-deoxy-β-D-glucopyranosyl)-N-tetradecyl-N'-dodecyl-urea
M.178 N-(2-L-leucinamido-2-deoxy-β-D-glucopyranosyl)-N-tetradecyl-N'-octadecyl-urea
M.179 N-(2-L-leucinamido-2-deoxy-β-D-glucopyranosyl)-N-octadecyl-N'-dodecyl-urea
M.180 N-(2-L-leucinamido-2-deoxy-β-D-glucopyranosyl)-N-octadecyl-N'-tetradecyl-urea
M.181 N-(2-L-leucinamido-2-deoxy-β-D-glucopyranosyl)-N-octadecyl-N'-octadecyl-urea
M.182 N-(2-glycinamido-2-deoxy-β-D-galactopyranosyl)-N-dodecyl-N'-dodecyl-urea M.183 N-(2-glycinamido-2-deoxy-β-D-galac-topyranosyl)-N-dodecyl-N'-tetradecyl-urea
M.184 N-(2-glycinamido-2-deoxy-β-D-galac-topyranosyl)-N-dodecyl-N'-octadecyl-urea
M.185 N-(2-glycinamido-2-deoxy-β-D-galac-topyranosyl)-N-tetradecyl-N'-dodecyl-urea
M.186 N-(2-glycinamido-2-deoxy-β-D-galac-topyranosyl)-N-tetradecyl-N'-octadecyl-urea
M.187 N-(2-glycinamido-2-deoxy-β-D-galac-topyranosyl)-N-octadecyl-N'-dodecyl-urea
M.188 N-(2-glycinamido-2-deoxy-β-D-galac-topyranosyl)-N-octadecyl-N'-tetradecyl-urea
M.189 N-(2-glycinamido-2-deoxy-β-D-galac-topyranosyl)-N-octadecyl-N'-octadecyl-urea Physical Data All the chemical reactions were followed by thin-layer chromatography. The reported $R_F$ values were determined on silica gel 60 thin-layer plates (E. Merck, Darmstadt). The composition of the mobile phase mixtures is reported in parts by volume.

Optical rotations were determined with a Perkin-Elmer type 241 polarimeter in 1 dm cells at 589 nm (Na-D line). The concentration C of the substance in the solvent is reported in percent (weight/volume). The elemental analyses in the indicated cases provided satisfactory figures for C, H and N, with the following limits of error
C ± 0.38%
H ± 0.31%
N ± 0.52%

Data for the glycosylamines of the general structure IV prepared by method A $R_F$ values in dichloromethane/methanol = 5:1
2-benzyloxycarbonylamino-2-deoxy-D-glucopyranose $R_F = 0.31$ 2-benzyloxycarbonylamino-2-deoxy-D-galac-topyranose $R_F = 0.29$ The glycosylamines of the structure IV which were prepared had very similar $R_F$ values in the abovementioned mobile phase, being in the range 0.46 to 0.49. Those glycosylamines with shorter alkyl chains had lower $R_F$ values than the glycosylamines with longer alkyl chains.

| Examples: | Compound | $R_F$ |
|---|---|---|
| | A 2 | 0.47 |
| | A 3 | 0.47 |
| | A 4 | 0.47 |
| | A 6 | 0.49 |
| | A 9 | 0.46 |
| | A 12 | 0.48 |

Data for the compounds of the general structure VI (X=—CH$_2$—) prepared by method B $R_F$ values in dichloromethane/methanol = 10:1

| Compound | $R_F$ | Elemental analysis |
|---|---|---|
| B 3 | 0.37 | |
| B 6 | 0.38 | $C_{38}H_{66}N_2O_7$ |
| B 8 | 0.38 | |
| B 9 | 0.39 | $C_{44}H_{78}N_2O_7$ |
| B 10 | 0.38 | $C_{40}H_{70}N_2O_7$ |
| B 12 | 0.38 | $C_{44}H_{78}N_2O_7$ |
| B 13 | 0.38 | $C_{46}H_{82}N_2O_7$ |
| B 16 | 0.38 | $C_{42}H_{74}N_2O_7$ |
| B 20 | 0.38 | $C_{44}H_{78}N_2O_7$ |
| B 21 | 0.38 | $C_{46}H_{82}N_2O_7$ |
| B 23 | 0.38 | $C_{50}H_{90}N_2O_7$ |
| B 25 | 0.34 | $C_{38}H_{66}N_2O_7$ |
| B 26 | 0.35 | $C_{40}H_{70}N_2O_7$ |
| B 27 | 0.36 | $C_{44}H_{78}N_2O_7$ |
| B 30 | 0.36 | $C_{46}H_{82}N_2O_7$ |
| B 31 | 0.36 | |
| B 33 | 0.37 | $C_{50}H_{90}N_2O_7$ |

Data for the compounds of the general structure IX (X=—CH$_2$—) prepared by method C $R_F$ values in toluene/ethanol = 20:1

| Comp. | $R_F$ | Elemental analysis | Melting point | $(\alpha)_D$ |
|---|---|---|---|---|
| C 1 | 0.36 | $C_{44}H_{72}N_2O_{10}$ | | +15.6° (C = 1.0; THF) |
| C 2 | 0.36 | $C_{46}H_{76}N_2O_{10}$ | 73° | +14.1° C = 1,0; THF) |
| C 6 | 0.36 | $C_{52}H_{88}N_2O_{10}$ | | |
| C 7 | 0.36 | $C_{50}H_{84}N_2O_{10}$ | 65° | +13.5° (G = 1.0; CH$_2$Cl$_2$) |
| C 9 | 0.36 | | | |
| C 10 | 0.33 | $C_{50}H_{84}N_2O_{10}$ | | |
| C 12 | 0.33 | $C_{52}H_{88}N_2O_{10}$ | | |

Data for the compounds of the general structure VI (X=—O—) prepared by method E $R_F$ values in dichloromethane/methanol = 10:1

| Comp. | $R_F$ | Elemental analysis |
|---|---|---|
| E 1 | 0.36 | $C_{39}H_{68}N_2O_8$ |
| E 3 | 0.36 | $C_{45}H_{80}N_2O_8$ |
| E 4 | 0.36 | |
| E 6 | 0.36 | $C_{44}H_{80}N_2O_8$ |
| E 8 | 0.36 | $C_{50}H_{92}N_2O_8$ |
| E 9 | 0.33 | $C_{39}H_{68}N_2O_8$ |
| E 11 | 0.33 | $C_{45}H_{80}N_2O_8$ |
| E 15 | 0.34 | $C_{47}H_{84}N_2O_8$ |
| E 17 | 0.34 | $C_{47}H_{84}N_2O_8$ |

Data for the compounds of the general structure VI (X=—NH—) prepared by method F $R_F$ values in dichloromethane/methanol = 10:1

| Comp. | $R_F$ | Elemental analysis |
|---|---|---|
| F 1 | 0.30 | $C_{39}H_{69}N_3O_7$ |
| F 3 | 0.30 | $C_{45}H_{81}N_3O_7$ |
| F 5 | 0.30 | $C_{47}H_{85}N_3O_7$ |
| F 6 | 0.30 | $C_{45}H_{81}N_3O_7$ |
| F 8 | 0.31 | $C_{51}H_{93}N_3O_7$ |
| F 9 | 0.28 | |
| F 14 | 0.28 | $C_{47}H_{85}N_3O_7$ |
| F 16 | 0.28 | $C_{47}H_{85}N_3O_7$ |

Data for the compounds of the general structure (X=—CH$_2$—) prepared by general method G R$_F$ values in dichloromethane/methanol1/25% aqueous ammonia=10:1.5:0.1

| Comp. | R$_F$ | Elemental analysis | $(\alpha)_D$ |
|---|---|---|---|
| G 1 | 0.31 | C$_3$H$_{60}$N$_2$O$_5$ × C$_2$H$_4$O$_2$ | +12.0°; C = 1.0; THF |
| G 2 | 0.31 | C$_{32}$H$_{64}$N$_2$O$_5$ × C$_2$H$_4$O$_2$ | |
| G 3 | 0.32 | | |
| G 4 | 0.33 | C$_{36}$H$_{72}$N$_2$O$_5$ × C$_2$H$_4$O$_2$ | |
| G 5 | 0.31 | C$_{32}$H$_{64}$N$_2$O$_5$ × C$_2$H$_4$O$_2$ | +11.3°; C = 1.0; THF |
| G 8 | 0.32 | C$_{38}$H$_{76}$N$_2$O$_5$ × C$_2$H$_4$O$_2$ | +8.5°; C = 1.0; THF |
| G 10 | 0.33 | C$_{36}$H$_{72}$N$_2$O$_5$ × C$_2$H$_4$O$_2$ | |
| G 13 | 0.32 | C$_{36}$H$_{72}$N$_2$O$_5$ × C$_2$H$_4$O$_2$ | +9.7°; C = 1.0; THF |
| G 14 | 0.33 | C$_{38}$H$_{76}$N$_2$O$_5$ × C$_2$H$_4$O$_2$ | |
| G 15 | 0.34 | C$_{40}$H$_{80}$N$_2$O$_5$ × C$_2$H$_4$O$_2$ | |
| G 16 | 0.34 | C$_{42}$H$_{84}$N$_2$O$_5$ × C$_2$H$_4$O$_2$ | +7.0°; C = 1.0; THF |
| G 17 | 0.29 | C$_{30}$H$_{60}$N$_2$O$_5$ × C$_2$H$_4$O$_2$ | +24.0°; C = 1.0; THF |
| G 19 | 0.29 | C$_{36}$H$_{72}$N$_2$O$_5$ × C$_2$H$_4$O$_2$ | +21.8°; THF |
| G 22 | 0.29 | C$_{36}$H$_{72}$N$_2$O$_5$ × C$_2$H$_4$O$_2$ | |
| G 24 | 0.31 | C$_{42}$H$_{84}$N$_2$O$_5$ × C$_2$H$_4$O$_2$ | +17.3°; C = 1.0; THF |

Data for the compounds of the general structure X (X=—O—) prepared by general method H R$_F$ values in dichloromethane/methanol/25% aqueous ammonia=10:1.5:0.1

| Comp | R$_F$ | Elemental analysis | $(\alpha)_D$ |
|---|---|---|---|
| H 2 | 0.30 | C$_{33}$H$_{66}$N$_2$O$_6$ × C$_2$H$_4$O$_2$ | +8.4°; C = 1.0, THF |
| H 6 | 0.30 | | |
| H 8 | 0.32 | C$_{43}$H$_{86}$N$_2$O$_6$ × C$_2$H$_4$O$_2$ | |
| H 11 | 0.26 | | |

Data for the compounds of the general structure X (X=—NH—) prepared by general method I R$_F$ values in dichloromethane/methanol/25% aqueous ammonia=10:1.5:0.1

| Comp. | R$_F$ | Elemental analysis |
|---|---|---|
| I 1 | 0.26 | C$_{31}$H$_{63}$N$_3$O$_5$ × C$_2$H$_4$O$_2$ |
| I 3 | 0.28 | |
| I 5 | 0.28 | C$_{39}$H$_{79}$N$_3$O$_5$ × C$_2$H$_4$O$_2$ |
| I 11 | 0.24 | C$_{37}$H$_{75}$N$_3$O$_5$ × C$_2$H$_4$O$_2$ |
| I 13 | 0.24 | |

Data for the compounds of the general structure XII (X=—CH$_2$—) prepared by general method J R$_F$ values in dichloromethane/methanol/25% aqueous ammonia=10:1.5:0.1

| Comp. | R$_F$ | Elemental analysis |
|---|---|---|
| J 1 | 0.33 | C$_{40}$H$_{69}$N$_3$O$_8$ |
| J 3 | 0.35 | C$_{44}$H$_{77}$N$_3$O$_8$ |
| J 4 | 0.35 | C$_{46}$H$_{81}$N$_3$O$_8$ |
| J 5 | 0.35 | C$_{42}$H$_{73}$N$_3$O$_8$ |
| J 7 | 0.35 | C$_{46}$H$_{81}$N$_3$O$_8$ |
| J 8 | 0.36 | C$_{48}$H$_{85}$N$_3$O$_8$ |
| J 10 | 0.36 | C$_{46}$H$_{81}$N$_3$O$_8$ |
| J 12 | 0.37 | C$_{50}$H$_{89}$N$_3$O$_8$ |
| J 13 | 0.36 | C$_{46}$H$_{81}$N$_3$O$_8$ |
| J 16 | 0.38 | C$_{52}$H$_{93}$N$_3$O$_8$ |
| J 17 | 0.34 | C$_{41}$H$_{71}$N$_3$O$_8$ |
| J 18 | 0.34 | C$_{43}$H$_{75}$N$_3$O$_8$ |
| J 20 | 0.35 | C$_{47}$H$_{83}$N$_3$O$_8$ |
| J 21 | 0.34 | C$_{43}$H$_{75}$N$_3$O$_8$ |
| J 23 | 0.35 | C$_{47}$H$_{83}$N$_3$O$_8$ |

-continued

| Comp. | R$_F$ | Elemental analysis |
|---|---|---|
| J 25 | 0.36 | C$_{45}$H$_{79}$N$_3$O$_8$ |
| J 29 | 0.37 | C$_{47}$H$_{83}$N$_3$O$_8$ |
| J 31 | 0.38 | C$_{51}$H$_{91}$N$_3$O$_8$ |
| J 34 | 0.43 | C$_{47}$H$_{83}$N$_3$O$_8$ |
| J 36 | 0.44 | C$_{49}$H$_{76}$N$_3$O$_8$ |
| J 37 | 0.45 | C$_{47}$H$_{83}$N$_3$O$_8$ |
| J 38 | 0.45 | C$_{49}$H$_{87}$N$_3$O$_8$ |
| J 41 | 0.55 | C$_{53}$H$_{87}$N$_3$O$_8$ |
| J 43 | 0.56 | C$_{55}$H$_{91}$N$_3$O$_8$ |
| J 45 | 0.55 | C$_{55}$H$_{91}$N$_3$O$_8$ |
| J 47 | 0.48 | C$_{43}$H$_{75}$N$_3$O$_8$ |
| J 50 | 0.51 | C$_{51}$H$_{91}$N$_3$O$_8$ |
| J 51 | 0.51 | C$_{49}$H$_{87}$N$_3$O$_8$ |
| J 54 | 0.54 | C$_{44}$H$_{77}$N$_3$O$_8$ |
| J 55 | 0.56 | C$_{46}$H$_{81}$N$_3$O$_8$ |
| J 57 | 0.57 | C$_{50}$H$_{89}$N$_3$O$_8$ |
| J 58 | 0.54 | C$_{46}$H$_{81}$N$_3$O$_8$ |
| J 60 | 0.57 | C$_{50}$H$_{89}$N$_3$O$_8$ |
| J 61 | 0.58 | C$_{52}$H$_{93}$N$_3$O$_8$ |
| J 63 | 0.57 | C$_{50}$H$_{89}$N$_3$O$_8$ |
| J 66 | 0.58 | C$_{50}$H$_{89}$N$_3$O$_8$ |
| J 69 | 0.59 | C$_{56}$H$_{101}$N$_3$O$_8$ |
| J 71 | 0.42 | C$_{47}$H$_{83}$N$_3$O$_8$ |
| J 74 | 0.42 | C$_{47}$H$_{83}$N$_3$O$_8$ |
| J 75 | 0.42 | C$_{49}$H$_{87}$N$_3$O$_8$ |
| J 77 | 0.35 | C$_{48}$H$_{77}$N$_3$O$_9$ |
| J 79 | 0.35 | C$_{50}$H$_{81}$N$_3$O$_9$ |
| J 80 | 0.37 | C$_{56}$H$_{93}$N$_3$O$_9$ |
| J 84 | 0.54 | C$_{52}$H$_{88}$N$_4$O$_{10}$ |
| J 86 | 0.55 | C$_{54}$H$_{88}$N$_4$O$_{10}$ |
| J 88 | 0.55 | C$_{58}$H$_{96}$N$_4$O$_{10}$ |
| J 90 | 0.57 | C$_{64}$H$_{108}$N$_4$O$_{10}$ |
| J 91 | 0.58 | C$_{49}$H$_{77}$N$_3$O$_{10}$ |
| J 92 | 0.58 | C$_{55}$H$_{89}$N$_3$O$_{10}$ |
| J 96 | 0.60 | C$_{57}$H$_{93}$N$_3$O$_{10}$ |
| J 98 | 0.48 | C$_{50}$H$_{79}$N$_3$O$_{10}$ |
| J 99 | 0.50 | C$_{56}$H$_{91}$N$_3$O$_{10}$ |
| J 102 | 0.51 | C$_{56}$H$_{91}$N$_3$O$_{10}$ |
| J 103 | 0.51 | C$_{58}$H$_{95}$N$_3$O |
| J 105 | 0.28 | C$_{40}$H$_{69}$N$_3$O$_8$ |
| J 109 | 0.30 | C$_{46}$H$_{81}$N$_3$O$_8$ |
| J 116 | 0.32 | C$_{47}$H$_{83}$N$_3$O$_8$ |
| J 122 | 0.54 | C$_{52}$H$_{93}$N$_3$O$_8$ |
| J 123 | 0.54 | C$_{50}$H$_{89}$N$_3$O$_8$ |
| J 124 | 0.54 | C$_{52}$H$_{93}$N$_3$O$_8$ |

Compounds of the general structure XII (X=—O—)

| Comp. | R$_F$ | Elemental analysis |
|---|---|---|
| J 127 | 0.31 | C$_{43}$H$_{75}$N$_3$O$_9$ |
| J 131 | 0.34 | C$_{47}$H$_{83}$N$_3$O$_9$ |
| J 133 | 0.35 | C$_{53}$H$_{95}$N$_3$O$_9$ |
| J 135 | 0.32 | C$_{44}$H$_{77}$N$_3$O$_9$ |
| J 139 | 0.34 | C$_{48}$H$_{85}$N$_3$O$_9$ |
| J 143 | 0.53 | C$_{47}$H$_{83}$N$_3$O$_9$ |
| J 147 | 0.55 | C$_{51}$H$_{91}$N$_3$O$_9$ |
| J 149 | 0.58 | C$_{57}$H$_{103}$N$_3$O$_9$ |
| J 151 | 0.27 | C$_{43}$H$_{75}$N$_3$O$_9$ |
| J 152 | 0.28 | C$_{47}$H$_{83}$N$_3$O$_9$ |

Compounds of the general structure XII (X=—NH—)

| Comp. | R$_F$ | Elemental analysis |
|---|---|---|
| J 158 | 0.29 | C$_{41}$H$_{72}$N$_4$O$_8$ |
| J 160 | 0.32 | C$_{47}$H$_{84}$N$_4$O$_8$ |
| J 162 | 0.32 | C$_{49}$H$_{88}$N$_4$O$_8$ |
| J 170 | 0.32 | C$_{50}$H$_{90}$N$_4$O$_8$ |
| J 174 | 0.50 | C$_{45}$H$_{80}$N$_4$O$_8$ |
| J 176 | 0.53 | C$_{51}$H$_{92}$N$_4$O$_8$ |
| J 178 | 0.53 | C$_{53}$H$_{96}$N$_4$O$_8$ |
| J 184 | 0.26 | C$_{47}$H$_{84}$N$_4$O$_8$ |

-continued

| Comp. | $R_F$ | Elemental analysis |
|---|---|---|
| J 186 | 0.26 | $C_{49}H_{88}N_4O_8$ |

Data for the compounds of the general structure I ($X=-CH_2-$) prepared by general method M $R_F$ values in dichloromethane/methanol/25% aqueous ammonia = 10:3:0.4

| Comp. | $R_F$ | Elemental analysis | $(\alpha)_D$ |
|---|---|---|---|
| M 1 | 0.23 | $C_{32}H_{63}N_3O_6 \times C_2H_4O_2$ | +19.9°; C = 1.0, THF |
| M 3 | | $C_{36}H_{71}N_3O_6 \times C_2H_4O_2$ | |
| M 4 | | $C_{38}H_{75}N_3O_6 \times C_2H_4O_2$ | +12.4°; C = 1.0, THF |
| M 5 | 0.21 | $C_{34}H_{67}N_3O_6 \times C_2H_4O_2$ | |
| M 7 | | $C_{38}H_{75}N_3O_6 \times C_2H_4O_2$ | |
| M 8 | 0.26 | $C_{49}H_{79}N_3O_6 \times C_2H_4O_2$ | +12.5°; C = 1.0, HOAc |
| M 10 | | $C_{38}H_{75}N_3O_6 \times C_2H_4O_2$ | |
| M 12 | | $C_{42}H_{83}N_3O_6 \times C_2H_4O_2$ | |
| M 13 | 0.22 | $C_{38}H_{75}N_3O_6 \times C_2H_4O_2$ | +17.3°; C = 1.0; THF |
| M 16 | 0.23 | $C_{44}H_{87}N_3O_6 \times C_2H_4O_2$ | +12.5°; C = 1.0; THF |
| M 17 | 0.19 | $C_{33}H_{65}N_3O_6 \times C_2H_4O_2$ | |
| M 18 | | $C_{35}H_{69}N_3O_6 \times C_2H_4O_2$ | |
| M 20 | 0.21 | $C_{39}H_{77}N_3O_6 \times C_2H_4O_2$ | +20.0°; C = 1.0; THF |
| M 21 | | $C_{35}H_{69}N_3O_6 \times C_2H_4O_2$ | |
| M 23 | | $C_{39}H_{77}N_3O_6 \times C_2H_4O_2$ | |
| M 25 | 0.21 | $C_{37}H_{73}N_3O_6 \times C_2H_4O_2$ | |
| M 29 | | $C_{39}H_{77}N_3O_6 \times C_2H_4O_2$ | +19.7°; C = 1.0; THF |
| M 31 | 0.23 | $C_{43}H_{85}N_3O_6 \times C_2H_4O_2$ | |
| M 34 | | $C_{39}H_{77}N_3O_6 \times C_2H_4O_2$ | +12.6°; C = 1.0; THF |
| M 36 | | $C_{41}H_{81}N_3O_6 \times C_2H_4O_2$ | |
| M 37 | 0.17 | $C_{39}H_{77}N_3O_6 \times C_2H_4O_2$ | +18.3°; C = 1.0; THF |
| M 38 | | $C_{41}H_{81}N_3O_6 \times C_2H_4O_2$ | |
| M 41 | 0.63 | $C_{45}H_{81}N_3O_6 \times C_2H_4O_2$ | +9.5°; C = 1.0; THF |
| M 43 | | $C_{47}H_{85}N_3O_6 \times C_2H_4O_2$ | |
| M 45 | 0.63 | $C_{47}H_{85}N_3O_6 \times C_2H_4O_2$ | +10.1°; C = 1.0; THF |
| M 47 | 0.51 | $C_{35}H_{69}N_3O_6 \times C_2H_4O_2$ | |
| M 50 | | $C_{43}H_{89}N_3O_6 \times C_2H_4O_2$ | |
| M 51 | 0.49 | $C_{41}H_{85}N_3O_6 \times C_2H_4O_2$ | +17.3°; C = 1.0; DMF |
| M 54 | 0.47 | $C_{36}H_{71}N_3O_6 \times C_2H_4O_2$ | +17.6°; C = 1.0; THF |
| M 55 | 0.47 | $C_{38}H_{75}N_3O_6 \times C_2H_4O_2$ | |
| M 57 | | $C_{42}H_{83}N_3O_6 \times C_2H_4O_2$ | |
| M 58 | 0.49 | $C_{38}H_{75}N_3O_6 \times C_2H_4O_2$ | +16.2°; C = 1.0; THF |
| M 60 | | $C_{42}H_{83}N_3O_6 \times C_2H_4O_2$ | |
| M 61 | 0.52 | $C_{44}H_{87}N_3O_6 \times C_2H_4O_2$ | +16.4°; C = 1.0; THF |
| M 63 | | $C_{42}H_{83}N_3O_6 \times C_2H_4O_2$ | |
| M 66 | 0.51 | $C_{42}H_{83}N_3O_6 \times C_2H_4O_2$ | +13.5°; C = 1.0; THF |
| M 69 | | $C_{48}H_{95}N_3O_6 \times C_2H_4O_2$ | |
| M 71 | | $C_{39}H_{77}N_3O_6 \times C_2H_4O_2$ | |
| M 74 | 0.27 | $C_{39}H_{77}N_3O_6 \times C_2H_4O_2$ | +9.6°; C = 1.0; THF |
| M 75 | | $C_{41}H_{81}N_3O_6 \times C_2H_4O_2$ | |
| M 77 | 0.19 | $C_{33}H_{65}N_3H_7 \times C_2H_4O_2$ | +3.8°; C = 1.0; THF |
| M 79 | | $C_{35}H_{69}N_3O_7 \times C_2H_4O_2$ | |
| M 80 | 0.22 | $C_{41}H_{81}N_3O_7 \times C_2H_4O_2$ | |
| M 84 | 0.01 | $C_{36}H_{72}N_4O_7 \times 2(C_2H_4O_2)$ | +15.7°; C = 1.0; THF |
| M 86 | | $C_{38}H_{76}N_4O_6 \times 2(C_2H_4O_2)$ | |
| M 88 | 0.01 | $C_{43}H_{84}N_4O_6 \times 2(C_2H_4O_2)$ | +15.5°; C = 1.0; THF |
| M 90 | | $C_{48}H_{96}N_4O_6 \times 2(C_2H_4O_2)$ | |
| M 91 | | $C_{34}H_{65}N_3O_8$ | |
| M 92 | 0.05 | $C_{49}H_{77}N_3O_8$ | +20.1°; C = 1.0; HOAc |
| M 96 | 0.04 | $C_{42}H_{81}N_3O_8$ | |
| M 98 | 0.02 | $C_{35}H_{67}N_3O_8$ | +15.9°; C = 1.0; HOAc |
| M 99 | | $C_{41}H_{79}N_3O_8$ | |
| M 102 | 0.02 | $C_{41}H_{79}N_3O_8$ | +15.4; C = 1.0; HOAc |
| M 103 | | $C_{32}H_{83}N_3O_8$ | |
| M 105 | 0.20 | $C_{32}H_{63}N_3O_6 \times C_2H_4O_2$ | +28.6°; C = 1.0; THF |
| M 109 | 0.21 | $C_{38}H_{75}N_3O_6 \times C_2H_4O_2$ | |
| M 166 | 0.21 | $C_{39}H_{77}N_3O_6 \times C_2H_4O_2$ | +30.4°; C = 1.0; THF |
| M 122 | 0.45 | $C_{44}H_{87}N_3O_6 \times C_2H_4O_2$ | |
| M 123 | 0.45 | $C_{32}H_{83}N_3O_6 \times C_2H_4O_2$ | +24.1°; C = 1.0; THF |
| M 124 | 0.45 | $C_{44}H_{87}N_3O_6 \times C_2H_4O_2$ | |

Compounds of the general structure I ($X=-O-$)

| Comp. | $R_F$ | Elemental analysis | $(\alpha)_D$ |
|---|---|---|---|
| M 127 | 0.20 | $C_{35}H_{69}N_3O_7 \times C_2H_4O_2$ | +18.1°; C = 1.0; THF |
| M 131 | 0.22 | $C_{39}H_{77}N_3O_7 \times C_2H_4O_2$ | |
| M 133 | 0.22 | $C_{45}H_{89}N_3O_7 \times C_2H_4O_2$ | |
| M 135 | 0.17 | $C_{36}H_{71}N_3O_7 \times C_2H_4O_2$ | +17.4°; C = 1.0; THF |
| M 139 | 0.19 | $C_{40}H_{79}N_3O_7 \times C_2H_4O_2$ | |
| M 143 | 0.44 | $C_{39}H_{77}N_3O_7 \times C_2H_4O_2$ | +16.4°; C = 1.0; THF |
| M 147 | 0.45 | $C_{43}H_{85}N_3O_7 \times C_2H_4O_2$ | |
| M 149 | 0.45 | $C_{38}H_{97}N_3O_7 \times C_2H_4O_2$ | |
| M 151 | 0.20 | $C_{35}H_{69}N_3O_7 \times C_2H_4O_2$ | +25.3°; C = 1.0; THF |
| M 152 | 0.20 | $C_{39}H_{77}N_3O_7 \times C_2H_4O_2$ | |
| M 158 | 0.19 | $C_{33}H_{66}N_4O_6 \times C_2H_4O_2$ | +14.2°; C = 1.0; THF |
| M 160 | 0.20 | $C_{39}H_{78}N_4O_6 \times C_2H_4O_2$ | |
| M 162 | 0.20 | $C_{41}H_{82}N_4O_6 \times C_2H_4O_2$ | |
| M 170 | 0.20 | $C_{42}H_{84}N_4O_6 \times C_2H_4O_2$ | |
| M 174 | 0.39 | $C_{37}H_{74}N_4O_6 \times C_2H_4O_2$ | |
| M 176 | 0.43 | $C_{43}H_{85}N_4O_6 \times C_2H_4O_2$ | |
| M 178 | 0.43 | $C_{45}H_{90}N_4O_6 \times C_2H_4O_2$ | |
| M 184 | 0.16 | $C_{39}H_{78}N_4O_6 \times C_2H_4O_2$ | |
| M 186 | 0.16 | $C_{41}H_{82}N_4O_6 \times C_2H_4O_2$ | |

It is understood that the specification and examples are illustrative but not limitative of the present invention and that other embodiments within the spirit and scope of the invention will suggest themselves to those skilled in the art.

We claim:

1. A compound of the formula

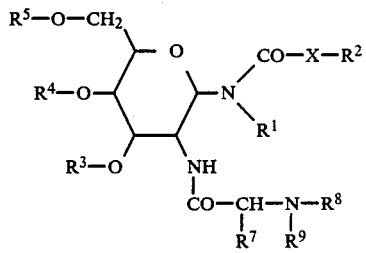

in which $R^1$ denotes hydrogen or a saturated or singly or multiply unsaturated alkyl radical having up to 50 carbon atoms, X represents $-CH_2-$, $-O-$ or $-NH-$, $R^2$ denotes a saturated or singly or multiply unsaturated alkyl radical having up to 50 carbon atoms, $R^3$, $R^4$ and $R^5$, independently of one another, denotes hydrogen or acetyl, benzoyl or P-nitro-benzoyl, $R^7$ denotes hydrogen, $C_1$-$C_7$-alkyl-, hydroxymethyl, 1-hydroxyethyl, mercaptomethyl, 2-(methylthio)-ethyl, 3-aminopropyl, 3-ureidopropyl, 3-guanidylpropyl, 4-aminobutyl, carboxymethyl, carbamylmethyl, 2-carboxyethyl, 2-carbamoylethyl, benzyl, 4-hydroxybenzyl, 3-indolylmethyl or 4-imidazolylmethyl, and $R^8$ represents hydrogen or methyl, and $R^9$ represents hydrogen, acetyl, benzoyl, trichloroacetyl, trifluoroacetyl, methoxycarbonyl, t-butyloxycarbonyl or benzyloxycarbonyl and $R^7$ and $R^8$ together can denote $-CH_2-CH_2-CH_2-$, or a pharmaceutically acceptable salt thereof.

2. A compound according to claim 1, in which $R^1$ represents a straight-chain or branched, saturated or unsaturated alkyl radical having 1 to 20 C atoms.

3. A compound according to claim 1, in which R² represents a straight-chain or branched, saturated or unsaturated alkyl radical having 8 to 20 C atoms.

4. A compound according to claim 1, in which the sugar residues are 2-amino-2-deoxy-D-glucose or 2-amino-2-deoxy-D-galactose.

5. A compound according to claim 1, in which the 2-amino group of the amino sugar is bonded to glycine, sarcosine, hippuric acid, alanine, valine, leucine, isoleucine, serine, threonine, cysteine, methionine, ornithine, citrulline, arginine, aspartic acid, aspargine, glutamic acid, glutamine, phenylalanine, tyrosine, proline, tryptophan or histidine, in the D- or L-form, or to an aminocarboxylic acid in the D- or L-form.

6. A compound according to claim 1, wherein such compound is N-(2-glycinamido-2-deoxy-β-D-glucopyranosyl)-N-dodecyl-dodecanoamide.

7. A compound according to claim 1, wherein such compound is N-(2-glycinamido-2-deoxy-β-D-glucopyranosyl)-N-dodecyl-actadecanoamide.

8. A compound according to claim 1, wherein such compound is N-(2-glycinamido-2-deoxy-β-D-glucopyranosyl)-N-tetradecyl-dodecanoamide.

9. A compound according to claim 1, wherein such compound is N-(2-L-alaninamido-2-deoxy-β-D-glucopyranosyl)-N-dodecyl-dodecanoamide.

10. A compound according to claim 1, wherein such compound is N-(2-D-alaninamido-2-deoxy-β-D-glucopyranosyl)-N-dodecyl-octadecanoamide.

11. A compound according to claim 1, wherein such compound is N-(2-L-phenylalaninamido-2-deoxy-β-D-glucopyranosyl)-N-dodecyl-octadecanoamide.

12. A compound according to claim 1, wherein such compound is N-(2-L-valinamido-2-deoxy-β-D-glucopyranosyl)-N-octadecyl-dodecanoamide.

13. A compound according to claim 1, wherein such compound is N-(2-L-valinamido-2-deoxy-β-D-glucopyranosyl)-N-octadecyl-tetradecanoamide.

14. A compound according to claim 1, wherein such compound is N-(2-L-leucinamido-2-deoxy-β-D-glucopyranosyl)-N-dodecyl-dodecanoamide.

15. A compound according to claim 1, wherein such compound is N-(2-L-leucinamido-2-deoxy-β-D-glucopyranosyl)-N-octadecyl-dodecanoamide.

16. A compound according to claim 1, wherein such compound is N-(2-sarcosinamido-2-deoxy-β-D-glucopyranosyl)-N-octadecyl-dodecanoamide.

17. A compound of the formula

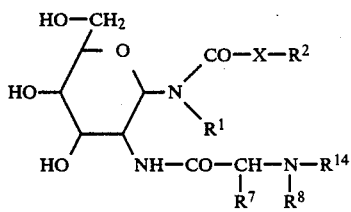

in which

R¹ denotes hydrogen or a saturated or singly unsaturated or singly or multiply unsaturated alkyl radical having up to 50 C atoms, X represents —CH₂, —O— or —NH—, R² denotes a saturated or singly or multiply unsaturated alkyl radical having up to 50 C atoms, R⁷ denotes hydrogen, C₁-C₇-alkyl, hydroxymethyl, 1-hydroxyethyl, mercaptomethyl, 2-(methylthio)-ethyl, 3-aminopropyl, 3-ureido-propyl, 3-guanidylpropyl, 4-aminobutyl, carboxymethyl, carbamoylmethyl, 2-carboxyethyl, 2-carbamoylethyl, benzyl, 4-hydroxybenzyl, 3-indolylmethyl or 4-imidazolylmethyl, R⁸ represents hydrogen or methyl, and R¹⁴ is a removable amino protective group.

18. An immunostimulating composition comprising an immunostimulating effective amount of a compound according to claim 1 and a pharmaceutically acceptable diluent.

19. A composition according to claim 18, wherein the diluent comprises a vaccine.

20. A composition according to claim 19, wherein the vaccine is a virus vaccine against influenza, mumps, measles, rubella, hepatitis or herpes.

21. A composition according to claim 19, wherein the vaccine is a virus vaccine against pseudorabies, rhinopneumonitis, Marek, foot-and-mouth and bovine influenza.

22. A method of stimulating the immune system which comprises administering to a patient an immunostimulating effective amount of a compound according to claim 1.

23. The method according to claim 22, wherein such compound is is
N-(2-glycinamido-2-deoxy-β-deoxy-β-D-glucopyranosyl)-N-dodecyl-dodecanoamide,
N-(2-glycinamido-2-deoxy-β-D-glucopyranosyl)-N-dodecyl-actadecanoamide,
N-(2-glycinamido-2-deoxy-β-D-glucopyranosyl)-N-tetradecyl-dodecanoamide,
N-(2-L-alaninamido-2-deoxy-β-D-glucopyranosyl)-N-dodecyl-dodecanoamide,
N-(2-D-alanimamido-2-deoxy-β-D-glucopyranosyl)-N-dodecyl-octadecanoamide,
N-(2-L-phenylalaninamido-2-deoxy-β-D-glucopyranosyl)-N-dodecyl-octadecanoamide,
N-(2-L-valinamido-2-deoxy-β-D-glucopyranosyl)-N-octadecyldodecanoamide,
N-(2-L-valinamido-2-deoxy-β-D-glucopyranosyl-N-octadecyl-tetradecanoamide,
N-(2-L-leucinamido-2-deoxy-β-D-glucopyranosyl)-N-dodecyl-dodecanoamide,
N-(2-L-leucinamido-2-deoxy-β-D-glucopyranosyl)-N-octadecyl-dodecanoamide or
N-(2-sarcosinamido-2-deoxy-β-D-glucopyranosyl)-N-octadecyl-dodecanoamide.

24. A method of treating a patient which comprises administering to such patient sisomicin or a vaccine plus an immunostimulating effective amount of a compound according to claim 1.

* * * * *